United States Patent [19]

Drummond et al.

[11] Patent Number: 5,041,378

[45] Date of Patent: Aug. 20, 1991

[54] PROCARYOTIC XYLOSE ISOMERASE MUTEINS

[75] Inventors: Robert J. Drummond, Richmond; Will Bloch, El Cerrito, both of Calif.; Brian W. Matthews, Eugene, Oreg.; Pamela L. Toy, Oakland, Calif.

[73] Assignees: Cetus Corporation, Emeryville, Calif.; Univerity of Oregon, Eugene, Oreg.

[21] Appl. No.: 84,479

[22] Filed: Aug. 11, 1987

[51] Int. Cl.$^5$ .................. C12N 9/92; C12N 15/09; C12N 15/52

[52] U.S. Cl. .................. 435/234; 435/69.1; 435/71.2; 435/91; 435/169; 435/172.3; 435/252.3; 435/320.1; 435/886; 536/27; 935/14; 935/29; 935/61; 935/72

[58] Field of Search ............ 435/70, 69.1, 71.2, 435/91, 169, 172.3, 234, 252-253, 320, 886; 536/27; 935/14, 29, 61, 72

[56] References Cited

U.S. PATENT DOCUMENTS

| 3,666,628 | 3/1971 | Dworschack et al. ........... 195/80 R |
| 3,826,714 | 10/1971 | Seukane et al. .................. 195/31 F |
| 4,410,627 | 10/1988 | Lloyd et al. . |
| 4,618,584 | 10/1986 | Johnson et al. ..................... 435/234 |

FOREIGN PATENT DOCUMENTS 0068647 1/1983 European Pat. Off. .
0130756 6/1984 European Pat. Off. .
0155832 3/1985 European Pat. Off. .

OTHER PUBLICATIONS

Kho, Yung Hee, 1985, *Chemical Abstracts*, vol. 103, Abstract No. 190868e.
Marcel et al., 1987 (Jun.) M66 208 (1/21:121-126).
Tewari et al., "Thermodynamics of the Conversion of Aqueous Glucose to Fructose", *Appld. Biochem and Biotech.*, 11:17-24 (1985).
Thomas et al., *Nature*, 318:375-576 (11/28/85), "Tailoring the pH Dependence of Enzyme Catalysis Using Protein Engineering".
Snow et al., (Abstr.) *Chem. Abstr.*, "Calculating Three-Dimensional Changes in Protein Structure Due to Amino-Acid Substitutions, the Variable Region of Immunoglobuline", vol. 106, Abstr. 117680v, p. 459 (1987).
Creighton, (Abstr), *Chem. Abstr.*, "Possible Implications of Many Proline Residues for the Kinetics of Protein Unfolding and Refolding", vol. 90, No. 9, Abstr. 68016y, p. 160 (1979).
Carrell et al., (Abstr.) *Chem. Abstr.*, "X-Ray Crystal Structure of D-Xylose Isomerase at 4-A resolution", vol. 100, Abstr. 135020k, p. 303 (1984).
Farber et al., (Abstr), Chem. Abstr., "The 3.0 A Crystal Structure of Xylose Isomerase from Streptomyces Olivochromogene", vol. 108, Abstr. 127608h, p. 365 (1988).
Henrick et al., (Abstr), *Chem. Abstr.*, "Comparison of Backbone Structures of Glucose Isomerase from Streptomyces and Arthrobacter", vol. 108, Abstr. 146202n, p. 351, (1988).
Matthews, Biochem., 26:6885-6887 (Nov. 1987).
Bryan, et al., J. Cellular Biochem., 1 Supple. 11C, (1987).
Sternberg, et al., Nature vol. 330, pp. 86-88 (Nov. 5, 1987).
Wells, et al., Proc. Natl. Acad. Sci. U.S.A., 84:1219-1223 (1987).

(List continued on next page.)

*Primary Examiner*—Robin L. Teskin
*Assistant Examiner*—Richard C. Peet
*Attorney, Agent, or Firm*—SaraLynn Mendel

[57] ABSTRACT

Xylose isomerase (XI) muteins useful in the conversion of glucose to fructose or xylose to xylulose are obtained in usable amounts by protein structural and recombinant DNA methods, including x-ray crystallography, cloning, computer graphic modeling and site-directed mutagenesis and expression of the bacterial DNA sequences encoding native procaryotic xylose isomerase. These native sequences are altered to encode the xylose isomerase muteins having improved catalytic function and/or thermostability.

1 Claim, 7 Drawing Sheets

OTHER PUBLICATIONS

Ahern, et al., Proc. Natl. Acad. Sci. U.S.A., 84:675–679 (1987).

Imanaka, et al., Nature vol. 324, pp. 695–697 (Dec. 18–25, 1986).

Villafranca, et al., Biochemistry, vol. 26, No. 8, 2182–2189 (1986).

Pantoliano, et al., Biochemistry, vol. 26, No. 8, 2077–2088 (1986).

Matsumura, et al., Nature vol. 323, pp. 356–358 (Sep. 25, 1986).

Sauer, et al., Biochemistry, vol. 25, No. 20, 5992–5998 (1986).

Pabo, et al., Biochemistry, vol. 25, No. 20 5987–5991 (1986).

Wells, et al., J. Biological Chem., vol. 261, 6564–70 (5/15/86).

Liao, et al., Proc. Natl. Acad. Sci. U.S.A., 83:576–580 (Feb. 1986).

Estell, et al., Jour. Biological Chem., 260:6518–6521 (6/10/85).

Craik, et al., Science, 228:291–297 (Apr. 19, 1985).

Perry; Wetzel, Science, vol. 226, 555–557 (Nov. 2, 1984).

Wilkinson, et al., Letters to Nature, 307:187–188 (1/12/84).

Kramer, et al., Nucleic Acids Research, 12:9441–0456 (11/24/84).

Messing, Meth. in Enzymology, 101:20–79 (1983).

Kuchinke, et al., EMBO Jour., 4:4:1067–1073 (1985).

Hecht, et al., Proc. Natl. Acad. Sci. U.S.A., 81:5685–5689 (1984).

Markland, et al., The Enzymes; 598–599 (1971), Ed. Paul Boyer, VIII, "Subtilisins: Primary Structure, Chemical & Physical Properties".

Stauffer, et al., Jour. Biological Chem., 244:5333–5338 (1969).

Matthews, et al., Proc. Natl. Acad. Sci. U.S.A. 84:6663–6667 (1987).

```
    ATGAACTACCAGCCCACCCCCGAGGACAGGTTCACCTTCGGACTGTGGACCGTCGGCTGG
  1 METAsnTyrGlnProThrProGluAspArgPheThrPheGlyLeuTrpThrValGlyTrp
    CAGGGACGGGACCCCTTCGGTGACGCCACGCGGCGCGCCCTCGACCCGGTCGAGTCGGTG
 21 GlnGlyArgAspProPheGlyAspAlaThrArgArgAlaLeuAspProValGluSerVal
    CGGCGGCTGGCCGAGCTGGGCGCCCACGGCGTCACGTTCCACGACGACGACCTCATCCCC
 41 ArgArgLeuAlaGluLeuGlyAlaHisGlyValThrPheHisAspAspAspLeuIlePro
    TTCGGCTCCAGCGACAGCGAGCGCGAGGAGCACGTCAAGCGGTTCCGGCAGGCGCTGGAC
 61 PheGlySerSerAspSerGluArgGluGluHisValLysArgPheArgGlnAlaLeuAsp
    GACACCGGCATGAAGGTGCCGATGGCCACCACCAACCTGTTCACCCACCCGGTGTTCAAG
 81 AspThrGlyMETLysValProMETAlaThrThrAsnLeuPheThrHisProValPheLys
    GACGGCGGCTTCACCGCCAACGACCGCGACGTGCGCCGCTACGCCCTGCGCAAGACCATC
101 AspGlyGlyPheThrAlaAsnAspArgAspValArgArgTyrAlaLeuArgLysThrIle
    CGCAACATCGACCTCGCGGTCGAGCTCGGCGCCGAGACCTATGTGGCCTGGGGCGGCCGC
121 ArgAsnIleAspLeuAlaValGluLeuGlyAlaGluThrTyrValAlaTrpGlyGlyArg
    GAGGGTGCCGAGTCGGGTGGCGCCAAGGACGTGCGGGACGCCCTCGACCGCATGAAGGAG
141 GluGlyAlaGluSerGlyGlyAlaLysAspValArgAspAlaLeuAspArgMETLysGlu
    GCCTTCGACCTGCTCGGCGAGTACGTCACCTCCCAGGGCTACGACATCCGCTTCGCCATC
161 AlaPheAspLeuLeuGlyGluTyrValThrSerGlnGlyTyrAspIleArgPheAlaIle
    GAGCCCAAGCCGAACGAGCCGCGCGGCGACATCCTGCTCCCCACCGTCGGCCACGCCCTG
181 GluProLysProAsnGluProArgGlyAspIleLeuLeuProThrValGlyHisAlaLeu
    GCGTTCATCGAGCGCCTGGAGCGACCGGAGCTGTACGGCGTGAACCCCGAGGTCGGCCAC
201 AlaPheIleGluArgLeuGluArgProGluLeuTyrGlyValAsnProGluValGlyHis
    GAGCAGATGGCCGGGCTGAACTTCCCGCACGGCATCGCGCAGGCGCTGTGGGCGGGCAAG
```

FIG. 2A

221  GluGlnMETAlaGlyLeuAsnPheProHisGlyIleAlaGlnAlaLeuTrpAlaGlyLys
     CTGTTCCACATCGACCTCAACGGCCAGAACGGCATCAAGTACGACCAGGACCTCCGCTTC
241  LeuPheHisIleAspLeuAsnGlyGlnAsnGlyIleLysTyrAspGlnAspLeuArgPhe
     GGCGCGGGCGACCTGCGGGCCGCGTTCTGGCTGGTGGACCTGCTGGAGTCGGCCGGCTAC
261  GlyAlaGlyAspLeuArgAlaAlaPheTrpLeuValAspLeuLeuGluSerAlaGlyTyr
     AGCGGCCCGCGGCACTTCGACTTCAAGCCGCCGCGGACCGAGGACTTCGACGGGGTGTGG
281  SerGlyProArgHisPheAspPheLysProProArgThrGluAspPheAspGlyValTrp
     GCCTCGGCGGCCGGCTGCATGCGCAACTACCTGATCCTCAAGGAGCGTGCGGCGGCCTTC
301  AlaSerAlaAlaGlyCysMETArgAsnTyrLeuIleLeuLysGluArgAlaAlaAlaPhe
     CGCGCCGACCCCGAGGTGCAGGAGGCGCTGCGCGCGTCCCGTCTGGACGAGCTGGCCCGG
321  ArgAlaAspProGluValGlnGluAlaLeuArgAlaSerArgLeuAspGluLeuAlaArg
     CCCACGGCGGCCGACGGTCTGCAGGCCCTGCTCGACGACCGGTCCGCCTTCGAGGAGTTC
341  ProThrAlaAlaAspGlyLeuGlnAlaLeuLeuAspAspArgSerAlaPheGluGluPhe
     GACGTCGACGCGGCGGCGGCCCGTGGGATGGCCTTCGAGCGCCTGGACCAGCTGGCGATG
361  AspValAspAlaAlaAlaAlaArgGlyMETAlaPheGluArgLeuAspGlnLeuAlaMET
     GACCACCTGCTGGGCGCCCGGGGCTGA
381  AspHisLeuLeuGlyAlaArgGly...

FIG. 2B

```
Sr GI      - S. rubiginosus Glucose Isomerase (1-)
Bs GI      - B. subtilis Glucose Isomerase (1-)
Amp GI     - A. spheroides Glucose Isomerase (1-)
Ec GI      - E. coli Glucose Isomerase (1-)

Sr GI       MNYQPTPEDRFTFGLWTVGWQGRDPFGDATRRALDPVESVRR-------LAELGA
Amp GI      MSLQATPDDKFSFGLWTVGWQARDAFGDATRPVLDPIEAVHK-------LAEIGA
Bs GI       -MAQSHSSSVNYFGSVNKVVFEGKASTNPLAFKYYNPQEVIGGKTMKEHLRFSIA
Ec GI       --------MQAYFDQLDRVRYEGSKSSNPLAFRHYNPDELVLGKRMEEHLRFAAC
Common              Q -      F                                    L Sr GI       HGVTFHDDDLIPFGSSDSER---------------------------------YE
Amp GI      YGVTFHDDDLVPFGADAATR---------------------------------DG
Bs GI       YWHTFTADGTDVFGAATMQRPWDHYKGMDLARARVEA--AFEMFEKLDAPFFAFHDR
Ec GI       YWHTFCWNGADMFGVGAFNRPWQQP-GEALALAKRKADVAFEFFHKLHVPFYCFHDV
Common        TF        FG    R Sr GI       HVKRFRQALDETGM----KVPMA---------------TTNLFTHPVFKDGGFTAN
Amp GI      IVAGFSKALDETGL----IVPMV---------------TTNLFTHPVFKDGGFTSN
Bs GI       DIAPEGSTLKETNQNLDIIVGMIKDYMRDSNVKLLWNTANMFTNPRFVHGAATSC
Ec GI       DVSPEGASLKEYINNFAQMVDVLAGKQEESGVKLLWGTANCFTNPRYGAGAATNP
Common           L E          V                    T N FT P    G  T Sr GI       DRDVRRYALRKTIRNIDLAVELGAETYVAWGGREGAESGGAKDVRDALDRMKEAF
Amp GI      DRSVRRYAIRKVLRQMDLGAELGAKTLVLWGGREGAEYDSAKDVGAALDRYREAL
Bs GI       NADVFAYAAAQVKKGLETAKELGAENYVFWGGREGYETLLNTDLKFELDNLARFM
Ec GI       DPEVFSWAATQVVTAMEATHKLGGENYVLWGGREGYETLLNTDLRQEREQLGRFM
Common         V    A                 LG   V WGGREG E       D Sr GI       DLLGEYVTSQGYDIRFAIEPKPNEPRGDILLPTVGHALAFIERLERPELYGVNPE
Amp GI      NLLAQYSEDQGYGLPFAIEPKPNEPRGDILLPTAGHAIAFVQELERPELFGINPE
Bs GI       HMAVDYAKEIEYTGQFLIEPKPKEPTTHQYDTDAATTIAFLKQYGLDNHFKLNLE
Ec GI       QMVVEHKHKIGFQGTLLIEPKPQEPTKHQYDYDAATVYGFLKQFGLEKEIKLNIE
Common                       IEPKP EP                F          N E
```

FIG. 3-1

```
Sr  GI    VGHEQMAGLNFPHGIAQALWAGKLFHIDLNGQNGIKYDQDLRFGAGDLRAAFWLV
Amp GI    TGHEQMSNLNFTQGIAQALWHKKLFHIDLNGQHGPKFDQDLVFGHGDLLNAFSLV
Bs  GI    ANHATLAGHTFEHELRMARVHGLLGSVDANQGHPLLGWDTDEFPTDLYSTTLAMW
Ec  GI    ANHATLAGHSFHHEIATAIALGLFGSVDANRGDAQLGWDTDQFPNSVEENALVMY
Common      H     F         A        D N              F Sr  GI    DLLESAGYS-----GPRHFDFKPPRT--EDFDGVWASAAGCMRNYLILKERAAAF
Amp GI    DLLENGPDGGPAYDGPRHFDYKPSRT--EDFDGVWESAKDNIRMYLLLKERAKAF
Bs  GI    EILQNGGLGS----GGLNFDAKVRRSSFEPDDLVWAHIAGMDAFARGLKVAHK--
Ec  GI    EILKAGGFTT----GGLNFDAKVRRQSTDKYDLFYGHIGAMDTMALALKIAAR--
Common       L         G  FD K R      D                LK Sr  GI    RADPEVQE--ALRASRLDELARPTAADGLQA--LLDD---RSAFEEFDVDAAAARGM
Amp GI    RADPEVQA--ALAESKVDELRTPTLNPGETYADLLAD---RSAFEDYDADAVGAKGY
Bs  GI    -----------LIEDRVFEDVIQHRYRSFTEGIGLEITEGRANFHTLEQYALNNKTI
Ec  GI    -----------MIEDGELDKRIAQRYSGWNSELGQQILKGQMSLADLAKYAQEHHLS
Common                                                      A Sr  GI    AFERLDQLAMDHLLGARG----
Amp GI    GFVKLNQLAIDHLLGAR-----
Bs  GI    KNE-SGRQERLKPILNQ-----
Ec  GI    PVHQSGRQEQLENLVNHYLFDK
Common
```

[1] Wilheim et al., Nuc. Acids Res. 13: 5717-5722 (1985);

[2] Saari et al., J. Bacter. 169: 612-618 (1987);

[3] Lawlis et al., Appl. and Env. Biol. 47: 15-21 (1984).

FIG. 3-2

PROCARYOTIC XYLOSE ISOMERASE MUTEINS

FIELD OF THE INVENTION

This invention relates to improved mutant forms of an industrially valuable enzyme and to site-specific mutations to direct microbial production of these forms More specifically, the invention relates to mutated procaryotic xylose isomerases with improved stability and/or catalytic activity.

BACKGROUND OF THE INVENTION

The conversion of glucose to fructose by the enzyme xylose isomerase is an important industrial process because fructose is sweeter to human taste than an equivalent amount of glucose or sucrose. Fructose has nutritional advantages over glucose or sucrose as a sweetener because less fructose is needed to impart a desired level of sweetness, and because it does not support the growth of the bacteria responsible for dental plaque as well as does sucrose which is the only economically competitive sweetener. However, the maximum exploitation of these benefits depends on rendering fructose economically competitive with alternative sweeteners, by devising the least expensive process for manufacturing food-grade fructose.

Current industrial practice uses a single-step enzyme-catalyzed isomerization of glucose to an approximately equilibrated mixture of glucose and fructuse, known as high-fructose syrup. Using this process, at equilibrium, only approximately 50% of the glucose has been transformed (Tewari et al., *Appld. Bioch. and Biotech.* 11:17–24 (1985)). Because percentage conversion varies directly with temperature, the fructose yield, and potentially the process economics, benefit from performing industrial glucose isomerization at the highest practical temperature.

Enzymes which catalyze the isomerization of sugars, including glucose, have been isolated from various organisms, including *Bacillus subtilis, Escherichia coli, Ampullariella* species and several Streptomyces species. The Streptomyces enzyme commonly used for commercial fructose production is most accurately designated xylose isomerase (XI), because it has much higher activity in converting xylose to xylulose than turning glucose into fructose. For industrial use, the purified enzyme is immobilized by adsorption to a solid support packed into a column, or "reactor", through which a concentrated solution of glucose is passed at the highest feasible temperature. The enzyme near the reactor inlet experiences a high concentration of glucose and low concentration of fructose. The enzyme near the reactor outlet is exposed to approximately equal concentrations of glucose and fructose. At any level in the catalytic reactor, the isomerase catalytic rate (V) depends on glucose (S) and fructose (P) concentrations ([ ]) as indicated in the following rate equation:

$$V/[E]_o = \frac{k_{catf}[S]/K_S - k_{catr}[P]/K_P}{1 + [S]/K_S + [P]/K_P}$$

In this equation $[E]_o$ is the total enzyme concentration, $K_S$ is the Michaelis constant for glucose, $K_P$ is the Michaelis constant for fructose, and $V/[E]_o$ is the enzyme specific activity, an expression of the catalytic effectiveness per enzyme molecule. $k_{catf}$ and $k_{catr}$ report the intrinsic catalytic activities of the glucose-saturated and fructose-saturated enzyme active sites, respectively representing the maximum possible forward (glucose→fructose) and reverse (fructose→glucose) values of V/[E] for a given temperature and pH. $K_S$, $K_P$, $k_{catf}$, and $k_{catr}$, vary with temperature, generally increasing with increased temperature below the temperature range where conformational unfolding of the enzyme occurs. Although $K_S$ and $K_P$ do not necessarily equal the respective dissociation constants for glucose and fructose, they probably approximate the dissociation constants in the case of Streptomyces XI, and therefore are inversely related to the affinities of the enzyme for glucose and fructose substrates.

XI catalytic activity in the industrially relevant (forward) direction is enhanced by environmental or mutational changes which increase $k_{catf}$ or $K_P$ or decrease $k_{catr}$ or $K_S$, increase the intrinsic forward catalytic efficiency or affinity for glucose or decrease the intrinsic reverse catalytic efficiency or affinity of XI for fructose. Currently used industrial glucose isomerization processes do not produce the maximum possible (equilibrium) percent conversion of glucose to fructose because the reaction slows as equilibrium is approached. Improvements which permit closer approach to equilibrium by weakening the fructose-XI interaction or by strengthening glucose-XI binding can be as valuable as improvements which permit conversion at higher temperature, where the equilibrium percent conversion is greater.

The preceding rate equation implies that there are many ways to change $k_{catf}$, $k_{catr}$, $K_S$, or $K_P$ to get a net increase in $V/[E]_o$. Detrimental changes in one or more kinetic parameters can be outweighed by beneficial changes in others. Some combinations of changes would reduce net activity. Structural changes affecting activity will alter several or all of the parameters, not all of them favorably, for two reasons:

(a) The four kinetic parameters are inescapably linked through the Haldane relationship:

$Keq = [P]equilibrium/[S]equilibrium = k_{catf}K_P/k_{catr}K_S$

At a given temperature and pH, a change in one parameter must be accompanied by a balancing change in some combination of the others to preserve the value of $K_{eq}$, the equilibrium constant; and (b) The relatively few amino acid residues which line the xylose isomerase active site interact with glucose, fructose, and catalytic intermediates. These interactions determine the values of the four kinetic parameters. Changing any one active site residue will strengthen or weaken several of these interactions and therefore modify several parameters.

It is thus difficult to target a simple set of improvements in catalytic activity because a change which improves one parameter may have strongly damaging effects on others. However, atomic resolution i.e. x-ray crystallographic data on the xylose isomerase active site permits the selection of a limited number of protein structural changes to increase net catalytic activity, for example, by strengthening the binding of glucose or by weakening the binding of fructose.

Recently, computer-graphic examination of the active sites of enzymes other than XI has led to successful prediction of structural changes affecting $k_{cat}$, $K_m$, and substrate specificity for these enzymes (Wilkinson et al., *Nature* 307:187–188 (1984); and Craik et al., *Science* 228:291 (1985)).

In addition to identifying active site mutations that may improve kinetic parameters, computerized graphical examination of the atomic-resolution crystallographic data for XI also permits prediction of amino acid substitutions, insertions, or deletions to stabilize the enzyme toward conformational unfolding or inactivating chemical reactions. Following are several recent examples of structurally stablizing mutations accomplished by site-specific or random mutagenesis.

Replacement of a glycine residue located in an α-helix has conformationally stabilized a neutral proteinase, increasing the thermal melting temperature by several degrees centigrade (Imanaka et al., *Nature* 324:695 (1986)).

Replacement of amino acids in the hydrophobic core of a protein with aromatic residues such as tyrosine, especially at positions near preexisting clusters of aromatic side chains, has been shown to promote resistance to thermal inactivation in kanamycin nucleotidyl transferase (Liao et al., *Biochem.*, 83:576-580 (1986)), and phage Lambda repressor (Hecht et al., *Biochem.*, 81:5685-5689 (1984)).

The introduction of new disulfide bonds to create covalent crosslinks between different parts of a polypeptide has been used to improve the thermal stability of bacteriophage T4lysozyme (Perry et al., *Science* 226:555 (1984)), bacteriophage Lambda repressor (Sauer et al., *Biochem.*, 125:5992 (1986)), *E. coli* dihydrofolate reductase (Villafranca et al., *Biochem.*, 26:2182 (1987)), and subtilisin BPN' (Pantoliano et al., *Biochem.*, 2077-2083 (1987)). A recently developed computer program (Pabo et al., *Biochem.*, 25:5987-5991 (1986)) permits efficient scanning of the crystallographically determined three-dimensional structure of a protein to suggest those sites where insertion of two cysteines might lead to disulfide bonds which would not disrupt the larger-scale conformation while stabilizing the local conformation.

Deamidation of an asparagine residue near the intersubunit interface of a homodimeric protein (triose phosphate isomerase) promotes irreversible thermal denaturation of this enzyme. Replacement of this asparagine with isoleucine enhanced thermal stability (Ahern et al., *P.N.A.S. USA*, 84:675-679 (1987)).

Fusion of the subunits of the homotetramaric enzyme, β-galactosidase, by duplication and in-phase head-to-tail fusion of the structural gene for the enzyme, using a DNA polylinker coding for a number of additional amino acids, resulted in a protein that was more stable toward proteolysis and heat compared to the wild-type enzyme (Kuchinke et al., *EMBO J.*, 4(4):1067-1073 (1985)).

Another class of potentially inactivating reactions include oxidation of amino acid residues at or near the active site of an enzyme, leading to a loss or reduction in catalytic activity. For example, oxidation of a key methionine residue in the protein subtilisin has been shown to lead to loss of proteolytic activity (Markland et al., in *The Enzymes* (P. Boyer, ed.) Vol. III:561 Academic Press (1971)). Replacement of that methionine by a serine, alanine or leucine residue resulted in an oxidation-resistant mutant protein (Estell et al., *J. Biol. Chem.* 260:6518-6521 (1985)).

Recent studies also have shown that some amino acid substitutions may have cumulative beneficial effects on thermalstability of the protein subtilisin (Bryan et al., *J. Cellular Biochem Supc.* 11C (N305) (1987); Matsumura et al., Nature (Letters) 323:356-358 (1986)).

Classical mutation of bacteria using radiation or chemicals has been used to produce mutant strains having different properties including altered protein activity. However, selective improvement of the organisms or the proteins has not been realized due to the randomness of the mutation process, which also requires tedious selection and screening steps to identify organisms which may possess the desired characteristics. Furthermore, with random mutagenesis an undesirable property may result along with the characteristic sought in the mutation.

More recently, random mutagenesis has been replaced by sitespecific (also known as primer-directed) mutagenesis. Sitespecific mutagenesis permits substitution, deletion or insertion of selected nucleotide bases within a DNA sequence encoding a protein of interest using synthetic DNA oligonucleotides having the desired sequence. Recombinant DNA procedures are used to substitute the synthetic sequence for the target sequence to introduce the desired mutation. (See Craik et al., *Science*, 228:291 (1985) for a review of these procedures). Development of the M13 bacteriophage vectors (Messing, in *Methods in Enzymoloqy* 101:20-78 (1983)) permits cloning of DNA fragments into singlestranded circular recombinants capable of autonomous replication. A modification of site-specific mutagenesis, termed gapped circle mutagenesis, provides an improved method for selective mutagenesis using oligonucleotide primers (Kramer et al., *Nuc. Acids Res.*, 12:9441-9456 (1984)). Kits for carrying out sitespecific mutagenesis and the gapped circle method are commercially available.

Mutant xylose isomerases having characteristics which vary from native enzyme would be useful. In particular, mutant isomerases having enhanced oxidation and thermal stability would be useful to extend the commercial utility of the enzyme.

Unfortunately, unless proteins share regions of substantial sequence or structural homology, it is not possible to generalize among proteins to predict, based on beneficial mutation of one protein, precisely where the sequence encoding another protein should be changed to improve the performance of that protein. It is therefore generally necessary to undertake an analysis of the precise structural and functional features of the particular protein to be altered in order to determine which amino acids to alter to produce a desired result such as increased thermostability or catalytic activity.

The present invention provides mutated forms ("muteins") of enzymatically active procaryotic xylose isomerase. Analysis of the structure of *Streptomyces rubiginosus* xylose isomerase (XI) to select alterations encoding the enzyme to enhance stability and/or activity of the resulting XI muteins was undertaken. Site-specific mutagenesis of the sequence encoding the enzyme was designed to produce the muteins. Regions of structural homology between xylose isomerases from several microorganisms were identified.

SUMMARY OF THE INVENTION

Accordingly, the present invention provides muteins containing specific modifications of procaryotic xylose isomerase, and materials and methods useful in producing these proteins, as well as modified microorganisms and cell lines useful in their production. Other aspects of the invention include the expression constructs and products thereof for the modified xylose isomerases as well as cloning vectors containing the DNA encoding the modified xylose isomerases.

The DNA encoding the reference procaryotic xylose isomerase is modified using site-directed gapped circle mutagenesis enabling the generation of a change at a selected site within the coding region of the isomerase. By this method, a change is introduced into isolated DNA encoding procaryotic xylose isomerase which, upon expression of the DNA, results in substitution of at least one amino acid at a predetermined site in the xylose isomerase, or insertion of a polylinker peptide for fusing at least two subunits of the xylose isomerase protein.

The modified xylose isomerases of the invention may exhibit improved stability and/or catalytic activity, and may have varied $K_m$, $k_{cat}$, $K_S$ or $K_p$.

BRIEF DESCRIPTION OF THE DRAWING

FIG. 2 (A and B) shows the DNA sequence and DNA-deduced amino acid sequence of *Streptomyces rubiginosus* xylose isomerase used as the reference protein;

FIG. 3 is a comparison of the amino acid sequence of native reference *Streptomyces rubiginosus* XI with the amino acid sequences of native XI from other organisms;

DETAILED DESCRIPTION OF THE INVENTION

Definitions

Figure 1:
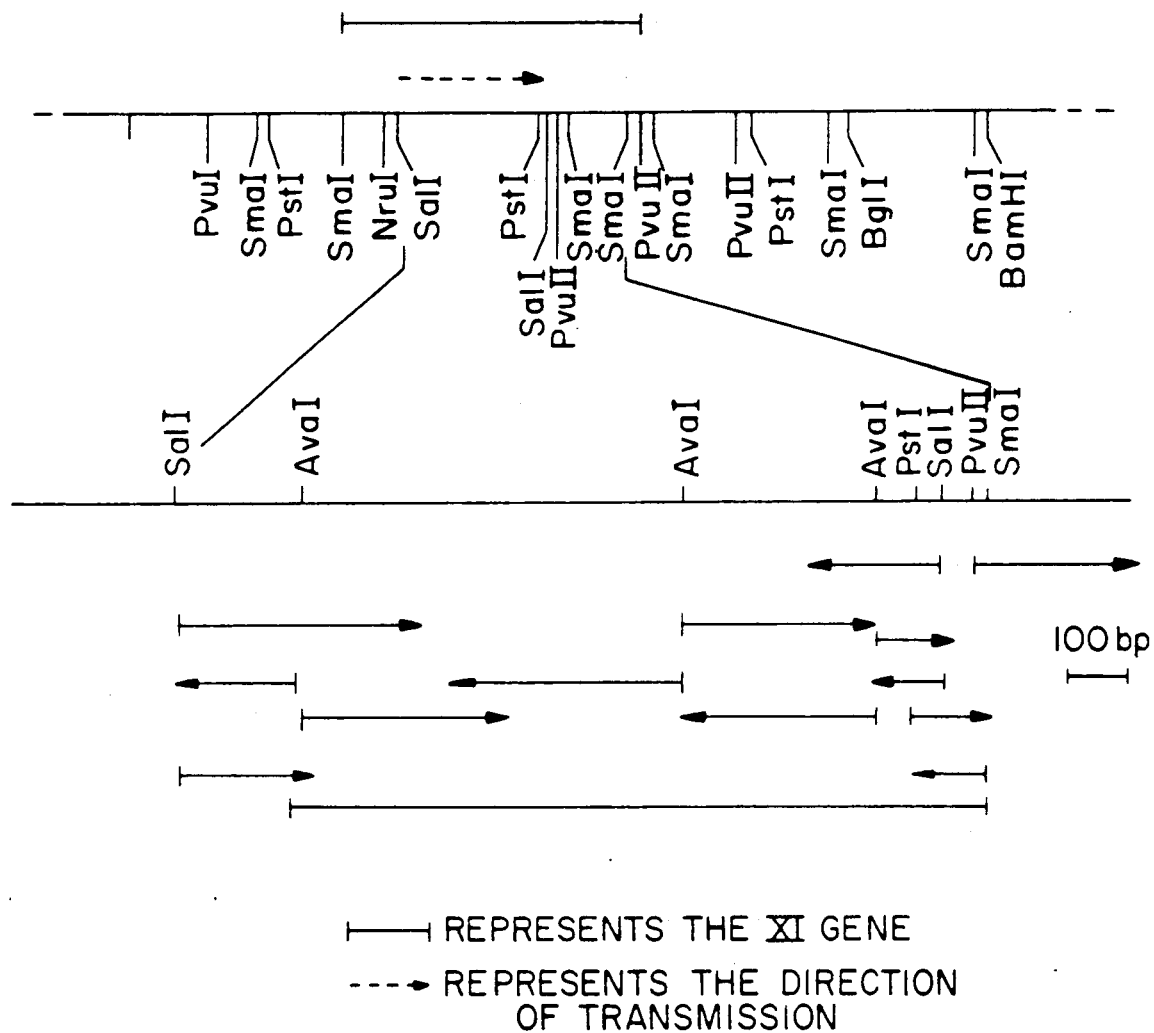
FIG. 1 is a restriction map of the XI gene and flanking region on the *Streptomyces rubiginosus* chromosome.

As used herein "reference" xylose isomerase ("XI") refers to the xylose isomerase encoded by a DNA sequence obtained from *Streptomyces rubiginosus* (S. rubiginosus) derived from ATCC strain 21,175 as described in U.S. Pat. No. 4,410,627, incorporated herein by reference. As used herein, XI is an enzyme having the characteristics of converting glucose to fructose and xylose to xylulose. Enzymes having this activity have an enzyme classification number of E.C.5.3.1.5.

"Mutein" in relation to the "reference" XI, refers to a protein having a related amino acid sequence which has enzymatic activity substantially the same as the reference XI in that the enzyme converts glucose to fructose and xylose to xylulose. However, it contains one or more amino acid substitutions, inversions, deletions or insertions for amino acid residues. These residues have been selected by predicting structural and chemical alterations that will result from particular substitutions at particular locations in the protein using x-ray crystallographic structural data for the reference XI. The term also includes a protein having an amino acid sequence related to the reference XI, but containing fused subunits.

"Expression vector" refers to a DNA construct containing a DNA sequence encoding XI, which is operably linked to a suitable control sequence capable of effecting the expression of said DNA in a suitable host. Such control sequences include a promoter to effect transcription, an optional operator sequence to control such transcription, a sequence encoding a suitable RNA ribosome binding site, and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. In the present specification, "plasmid" and "vector" are sometimes used interchangeably as the plasmid is the most common form of vector at present. However, the invention is intended to include such other forms of expression vectors which serve equivalent functions and which are, or become, known in the art.

"Recombinant host cells", "host cells", "cells", "cell cultures" and so forth are used interchangeably to designate individual cells, cell lines, cell cultures and harvested cells which have been or are intended to be transformed with the recombinant vectors of the invention. The terms also include the progeny of the cells originally receiving the vector.

"Transformed" refers to any process for altering the DNA content of the host, including in vitro transformation procedures as described below, phage infection, or such other means for effecting controlled DNA uptake as are known in the art.

"Operably linked" as used herein regarding DNA sequences or genes refers to the situation wherein the sequences or genes are juxtaposed in such a manner as to permit their ordinary functionality. For example, a promoter operably linked to a coding sequence refers to those linkages where the promoter is capable of controlling the expression of the sequence.

"Control sequences" refers to DNA sequences which control the expression of the sequence which encodes the mutein. Examples include promoters for transcription initiation, optionally with an operator, enhancer regions, ribosome binding site sequences and translation signals which initiate and terminate translation of the gene. Such control sequences must be compatible with, i.e., operable in, the host into which they will be inserted.

General Description

A number of naturally occurring xylose isomerases and their genes may be obtained from a variety of procaryotic organisms, such as *Bacillus subtilis*. *Ampullariella* species, both disclosed in U.S. Pat. No. 3,826,714, *S. rubiginosus* (ATCC 21,175 disclosed in U.S. Pat. Nos. 3,666,628 and 4,410,627) and *E. coli*. The foregoing patents are incorporated by reference herein. In addition, naturally occuring mutants of xylose isomerase may be employed as sources for genetic material for mutation.

The DNA sequence encoding the gene for *S. rubiginosus* xylose isomerase may be obtained and cloned in accord with the general method herein. As will be seen from the examples, this method includes determining at least a portion of the amino acid sequence for the enzyme, synthesizing labeled probes having putative sequences encoding sequenced regions of the xylose isomerase, preparing genomic DNA libraries prepared from chromosomal DNA isolated from *S. rubiginosus* cells expressing the isomerase, and screening the library for the gene encoding xylose isomerase by hybridization to the labeled probes. Positively hybridizing clones are then restriction enzyme mapped and sequenced.

Once the xylose isomerase gene has been identified and cloned, a number of modifications are undertaken to modify the gene to encode enzyme muteins with improved characteristics compared to the reference enzyme, for industrial uses. The reference enzyme is the enzyme prior to the modifications as described herein.

Crucial to selection of sites for mutagenesis is procurement of an atomic-resolution x-ray crystal structure of the reference enzyme. Computer graphics analysis of the enzyme's crystal structure allows the identification of specific sites for alteration that may result in muteins possessing improved properties.

To facilitate selection of the desired modifications, a strategy may be devised using a computer-based model-building system, for example using computer assistance such as the Proteus computer program described by Pabo et al., *Biochem.* 25:5987–5991 (1986), incorporated by reference herein. Generally, such methodology involves analyzing geometric aspects of protein structure revealed, for example, by x-ray diffraction crystallography. Preferably, such a strategy takes into account how the proposed modification will fit with the remaining (unmodified) portion of the protein, taking into consideration the environment of the amino acid residues.

After the desired modifications are selected, the DNA sequence encoding the xylose isomerase is site-specifically mutagenized to substitute nucleotides encoding selected amino acids at the predetermined positions within the sequence.

Site-specific mutagenesis (also known as primer-directed mutagenesis) is a technique which is well-established in the art. A preferred procedure is gapped circle mutagenesis (Kramer et al., *Nucl Acids Res.* 12:9441–9456 (1986)). In this method the DNA sequence encoding the gene to be mutagenized is ligated into an M13 vector having amber mutations which prevent its replication. The oligonucleotide primer incorporating the desired nucleotide changes is ultimately joined to a similar M13 vector lacking the mutation. The phage incorporating primer preferentially replicates in a susceptible host, thus enriching for the altered gene.

In general, site-specific mutagenesis is performed by cloning the DNA sequence encoding the reference enzyme into a convenient M13 cloning vector and using an appropriate primer, to convert a residue at an identified position for example, to a conservative amino-acid replacement. A synthetic oligonucleotide complementary, except in areas of limited mismatching to the desired sequence, is used as a primer in the synthesis of a strand complementary to the single-stranded reference isomerase sequence in the phage vector. The resulting double-stranded DNA is transformed into a phage-supporting host bacterium. Cultures of the transformed bacteria are plated in top agar, permitting plaque formation from single cells which harbor the phage. Theoretically, 50% of the plaques will consist of phage containing the mutant form; 50% will have the original sequence. Using the gapped circle method, the plaques will be enriched for phage having the mutant form. The plaques are hybridized with kinased synthetic primer under stringency conditions which permit hybridization only with the desired sequence which will form a perfect match with the probe. Hybridizing plaques are then picked and cultured, and the DNA is recovered.

The mutated cloned xylose isomerase genes may then be ligated into an expression vector (which may also be the cloning vector) with requisite regions for replication in the host. The vector is transfected into a host for enzyme synthesis, and the recombinant host cells are cultured under conditions favoring enzyme synthesis, usually selection pressure such as is supplied by the presence of an antibiotic, the resistance to which is encoded by the vector. Culture under these conditions results in enzyme yields multifolds greater than the wild type enzyme synthesis of the parent organism, even if it is the parent organism that is transformed.

The mutated cloned xylose isomerases are used to transform a host cell in order to express the mutated isomerase. In the preferred embodiment, the mutated xylose isomerase gene is ligated into a high copy number plasmid. This plasmid replicates in hosts in the sense that it contains the well-known elements necessary for plasmid replication: a promoter operably linked to the gene (which may be the gene's own homologous promoter if it is recognized, i.e., transcribed by the host), a transcription termination and polyadenylation region (necessary for stability of the mRNA transcribed by the host from the xylose isomerase gene) which is exogenous or is supplied by the endogenous terminator region of the isomerase gene and, preferably, a selection gene such as an antibiotic resistance gene that enables continuous growth in antibiotic-containing media. High copy number plasmids also contain an origin of replication compatible with the host, thereby enabling large numbers of plasmids to be generated in the cytoplasm without chromosomal limitations. However, it is within the scope of the invention herein to integrate multiple copies of the isomerase gene into the host genome. This is facilitated by bacterial strains that are particularly susceptible to homologous recombination. The resulting host cells are termed recombinant host cells.

Standard Methods

Most of the techniques which are used to transform cells, construct vectors, effect hybridization with probe, and the like as well as to perform x-ray crystallography of a protein, are widely practiced in the art, and most practitioners are familiar with the standard resource materials which describe specific conditions and procedures (see for example, Maniatis et al., Molecular Cloning: A Laboratory Manual, Cold Spring Harbor Press, Cold Spring Harbor, N.Y. (1982)). However, for convenience, the following paragraphs may serve as a guideline.

Control Sequences And Corresponding Hosts

Procaryotes most frequently are represented by various strains of *E. coli*. However, other microbial strains may also be used, such as bacilli for example, *Bacillus subtilis. Pseudomonas* sp., *Streptomyces rubiginosus:* various species of fungi or other microorganisms. In such procaryotic systems, plasmid vectors which contain replication sites and control sequences derived from a species compatible with the host are used. For example, *E. coli* is typically transformed using derivatives of pBR322, a plasmid derived from an *E. coli* species by Bolivar, et al., *Gene* 2:95 (1977). pBR322 contains genes for ampicillin and tetracycline resistance, and thus provides additional markers which can be either retained or destroyed in constructing the desired vector. Commonly used procaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang, et al., *Nature* (1977) 198:1056), the tryptophan (trp) promoter system (Goeddel, et al., *Nucleic Acids Res* (1980) 8:4057), and the lambda derived PL promoter and N-gene ribosome binding site (Shimatake, et al., *Nature* (1981) 292:128), which has been made useful as a portable control cassette. Also useful is the phosphatase A (phoA) system described by Chang, et al., in copending U.S. Ser. No. 715,653, filed Mar. 25, 1985, assigned to the same assignee and incorporated herein by reference. However, any available promoter system compatible with procaryotes can be used.

In addition to bacteria, eucaryotic microbes, such as yeast, may also be used as hosts. Laboratory strains of *Saccharomyces cerevisiae*, Baker's yeast, are frequently used, although a number of other strains are commonly available. Many plasmid vectors suitable for yeast expression are known. (See, for example, Stinchcomb, et al., *Nature* 282:39 (1979), Tschempe, et al., *Gene* 10:157 (1980) and Clarke, L., et al., *Meth. Enzymol.* 101:300 (1983)). Control sequences for yeast vectors include promoters for the synthesis of glycolytic enzymes (Hess, et al., *J. Adv. Enzyme. Reg.* 7:149 (1968); Holland, et al., *Biochemistry* 17:4900 (1978)). Additional promoters known in the art include the promoter for 3-phosphoglycerate kinase (Hitzeman, et al., *J. Biol. Chem.* 255:2073 (1980)), and those for other glycolytic enzymes, such as glyceraldehyde-3-phosphate dehydrogenase, hexokinase, pyruvate decarboxylase, phosphofructokinase, glucose-6-phosphate isomerase, 3 phosphoglycerate mutase, pyruvate kinase, triosephosphate isomerase, phosphoglucose isomerase, and glucokinase. Other promoters, which have the additional advantage of transcription controlled by growth conditions, are the promoter regions for alcohol dehydrogenase 2, isocytochrome C, acid phosphatase, degradative enzymes associated with nitrogen metabolism, and enzymes responsible for maltose and galactose utilization (Holland, ibid). It is also believed that terminator sequences are desirable at the 3' end of the coding sequences. Such terminators are found in the 3' untranslated region following the coding sequences in yeast-derived genes. Many of the vectors illustrated contain control sequences derived from the enolase gene containing plasmid peno 46 (Holland, M. J., et al., *J. Biol. Chem.* 256:1385 (1981)) or the LEU2 gene obtained from YEp13 (Broach, J., et al., *Gene* 8:121 (1978)), however, any vector containing a yeast compatible promoter, origin of replication and other control sequences is suitable.

It is also, of course, possible to express genes encoding polypeptides in eucaryotic host cell cultures derived from multicellular organisms. See, for example, *Tissue Culture*, Academic Press, Cruz and Patterson, editors (1973). Useful host cell lines include murine myelomas NS1, VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers, et al., *Nature* 273:113 (1978)), or other viral promoters such as those derived from polyoma, Adenovirus 2, bovine papiloma virus (BPV), or avian sarcoma viruses, or immunoglobulin promoters and heat shock promoters. This system is disclosed in U.S. Pat. No. 4,419,446. A modification of this system is described in U.S. Pat. No. 4,601,978. General aspects of mammalian cell host system transformations have been described by Axel; U.S. Pat. No. 4,399,216 issued Aug. 16, 1983. It now appears, also, that "enhancer" regions are important in optimizing expression; these are, generally, sequences found upstream of the promoter region. Origins of replication may be obtained, if needed, from viral sources. However, integration into the chromosome is a common mechanism for DNA replication in eucaryotes.

Plant cells are also now available as hosts, and control sequences compatible with plant cells such as the nopaline synthase promoter and polyadenylation signal sequences (Depicker, A., et al., *J. Mol. Appl. Gen.* 1:561 (1982)) are available.

Recently, in addition, expression systems employing insect cells utilizing the control systems provided by baculovirus vectors have been described (Miller, D. W., et al., in *Genetic Engineering*, Setlow, J. K., et al., eds., Plenum Publishing, Vol. 8, pp. 277-297 (1986)).

Transformations

Depending on the host cell used, transformation is done using standard techniques appropriate to such cells. The calcium treatment employing calcium chloride, as described by Cohen, S. N., *Proc. Natl. Acad. Sci. (USA)* 69:2110 (1972), is used for procaryotes or other cells which contain substantial cell wall barriers. Infection with *Agrobacterium tumefaciens* r (Shaw, C. H., et al., *Gene* 23:315 (1983)) is used for certain plant cells. For mammalian cells without such cell walls, the calcium phosphate precipitation method of Graham and van der Eb, *Virology* 52:546 (1978) is preferred. Transformations into yeast are carried out according to the method of Van Solingen, P., et al., *J. Bact.* 130:946 (1977) and Hsiao, C. L., et al., *Proc. Natl. Acad. Sci. (USA)* 76:3829 (1979).

Probe of cDNA or Genomic Libraries

"Southern Analysis" is a method by which the presence of DNA sequences in a digest or DNA-containing composition is confirmed by hybridization to a known, labeled oligonucleotide or DNA fragment. For the purposes herein, Southern Analysis shall mean separation of digests on 1 percent agarose and depurination as described by G. Wahl et al., *PNAS* (USA), 76:3683-3687 (1979), transfer to nitrocellulose by the method of E. Southern, *J. Mol. Biol.* 98:503-517 (1975), and hybridization as described by 25 Maniatis et al., *Cell*, 15:687-701 (1978).

cDNA or genomic libraries are screened using the colony or plaque hybridization procedure. Bacterial colonies, or the plaques for phage are lifted onto duplicate nitrocellulose filter papers (S & S type BA-85). The plaques or colonies are lysed and DNA is fixed to the filter by sequential treatment for 5 min with 500 mM NaOH, 1.5 M NaCl. The filters are washed twice for 5 min each time with 5×standard saline citrate (SSC) and are air dried and baked at 80° C. for 2 hr.

The gels for Southern blot or the duplicate filters for cDNA or genomic screening are prehybridized at 25°-42° C. for 6-8 hr with 10 ml per filter of DNA hybridization buffer without probe (0-50% formamide, 5-6×SSC, pH 7.0, 5×Denhardt's solution (polyvinylpyrrolidine, plus Ficoll and bovine serum albumin; 1× =0.02% of each), 20-50 mM sodium phosphate buffer at pH 7.0, 0.2% SDS, 20 μg/ml poly U (when probing cDNA), and 50 μg/ml denatured salmon sperm DNA). The samples are then hybridized by incubation at the appropriate temperature for about 24-36 hours using the hybridization buffer containing kinased probe (for oligomers). Longer cDNA or genomic fragment probes may be labeled by nick translation or by primer extension.

The conditions of both prehybridization and hybridization depend on the stringency desired, and vary, for example, with probe length. Typical conditions for relatively long (e.g., more than 30-50 nucleotide) probes employ a temperature of 42° C. and hybridization buffer containing about 20%-50% formamide. For the lower stringencies needed for oligomeric probes of about 15 nucleotides, lower temperatures of about 25°-42° C., and lower formamide concentrations (0%-20%) are employed. For longer probes, the filters may be washed, for example, four times for 30 minutes, each time at 40°-50° C. with 2×SSC, 0.2% SDS and 50 mM sodium phosphate buffer at pH 7, then washed twice with 0.2×SSC and 0.2% SDS, air dried, and are autoradiographed at −70° C. for 2 to 3 days. Washing conditions are somewhat less harsh for shorter probes.

Minor variations from these specified hybridization methods are described in the examples below.

Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site-specific DNA cleavage is performed by treating the DNA with the suitable restriction endonuclease(s) under conditions which are generally understood in the art, and the particulars of which are specified by the manufacturer of these commercially available restriction enzymes. See, e.g., New England Biolabs, Product Catalog (New England Biolabs, Beverly, Ma.). In general, about 1 μg of plasmid or DNA sequence is cleaved by one unit of enzyme in about 20 μl of buffer solution. An excess of restriction enzyme is typically used to insure complete digestion of the DNA substrate; however, it may be desirable to carry out partial digestions in which some but not all of the sites of a given restriction enzyme in the DNA are cleaved. Such partial digestions are accomplished by varying the concentration of restriction enzyme or length of time the restriction digestion is carried out. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations are found in *Methods in Enzymology* (1980) 65:499-560; Lawn et al., *Nucl. Acids Res.* 9:6113-6114 (1981) and Goeddel et al., *Nucl. Acids Res.* 8:4057 (1980)).

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM $MgCl_2$, 6 mM dTT, about 10 U/μl Klenow and 5-10 μM dNTPs. The Klenow fragment fills in at 5' sticky ends but chews back protruding 3' single strands, even though the four dNTPs are present. If desired, selective repair can be performed by supplying only one of the, or selected, dNTPs within the limitations dictated by the nature of the sticky ends.

After treatment with Klenow, the mixture is extracted with phenol/chloroform and ethanol precipitated. Treatment under appropriate conditions with S1 nuclease results in hydrolysis of any single-stranded portion.

Ligations are performed in 15-30 μl volumes under the following standard conditions and temperatures: 20 mM Tris-HCl, pH 7.5, 10 mM $MgCl_2$, 10 mM dTT, 33 μg/ml BSA, 10 mM-50 mM NaCl, and either 40 μM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 33-100 μg/ml total DNA concentrations (5-100 nM total end concentration). Intermolecular blunt end ligations (usually employing a 10-30 fold molar excess of linkers) are performed at 1 μM total ends concentration.

In vector construction employing "vector fragments", the vector fragment is commonly treated with bacterial alkaline phosphatase (BAP) in order to remove the 5' phosphate and prevent religation of the vector. BAP digestions are conducted at pH 8 in approximately 150 μM Tris, in the presence of $Na^+$ and $Mg^{+2}$ using about 1 unit of BAP per μg of vector at 60° C. for about one hour. In order to recover the nucleic acid fragments, the preparation is extracted with phenol/chloroform and ethanol precipitated. Alternatively, religation can be prevented in vectors which have been double digested by additional restriction enzyme digestion of the unwanted fragments.

Verification of Construction

In the constructions set forth below, correct ligations for plasmid construction are confirmed by first transforming *E. coli* strain MM294, or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, et al., *P.N.A.S. (USA)* 62:1159 (1969), optionally following chloramphenicol amplification (Clewell, *J. Bacteriol.* (1972) 110:667). The isolated DNA is analyzed by restriction and/or sequenced by the dideoxy method of Sanger, et al., *P.N.A.S. (U.S.A.)*, 74:5463 (1977) as further described by Messing, et al., *Nucleic Acids Res.* 9:309 (1981), or by the method of Maxam, et al., *Methods in Enzymology* 65:499 (1980).

Preparation of Synthetic Oligonucleotides for Modification of DNA

Synthetic oligonucleotides may be prepared by the triester method of Matteucci, et al., *J. Am. Chem. Soc.* 103:3185-3191 (1981), or using automated synthesis methods. Kinasing of single strands prior to annealing or for labeling is achieved using an excess, e.g., approximately 10 units of polynucleotide kinase to 1 nM substrate in the presence of 50 mM Tris, pH 7.6, 10 mM MgC12. 5 mM dithiothreitol, 1-2 mM ATP. If kinasing is for labeling of probe, the ATP will contain high specific activity 32YP. The synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Hosts Exemplified

Host strains that may be used in cloning and expression herein are as follows:

For cloning and sequencing, and for expression of the construction under control of most bacterial promoters, *E. coli* strain MM294 obtained from the American Type Culture Collection, Rockville, Md. (ATCC, No. 53,131) is used as the host. This particular strain contains a plasmid, pAW721, and should be plasmid cured prior to use. For expression under control of the trp promoter and trpE translation initiation signal in the expression vector pTRP3, *E. coli* strain MM294 or DG101, may be used. pTRP3 has been accepted for deposit under the terms of the Budapest Treaty, under accession No. ATCC 39,946.

For M13 phage recombinants *E. coli* strains susceptible to phage infection, such as *E. coli* K12 strain DG98 (ATCC No. 39,768) and HB2151 (commercially available from Anglican Biotechnology Ltd., Colchester, Essex, UK) are employed.

Mammalian expression may be performed in COS-7, COS-A2, CV-1, and murine cells, and insect cell based expression in *Spodoptera frugipeida*.

The mutant xylose isomerases expressed upon transformation of the suitable hosts have similar enzymatic activity to the reference xylose isomerase and are screened for those that exhibit desired characteristics, for example, kinetic parameters, oxidation stability, thermal stability and the like.

A change in kinetic parameters is defined as an alteration in $k_{catf}$, $k_{catr}$, $K_S$ and/or $K_p$. Procaryotic xylose isomerase muteins with increased or diminished $k_{catf}$, $k_{catr}$, $K_S$ or $K_p$ values may be obtained as described herein. Generally, the objective will be to obtain a mutein having a greater (numerically larger) $k_{cat}$ for the forward reactions (glucose to fructose, and xylose to xylulose), and a reduced (numerically smaller) $K_S$ for the substrates glucose or xylose, thereby enabling the use of the enzyme to more efficiently process its target substrate. $k_{cat}$ and $K_S$ are measured by known procedures, for example by analysis of the progress curve for these known parameters in the enzyme/substrate reaction. The rate of the reaction may be measured as a function of substrate concentration. Data are preferably analyzed by fitting to the Michaelis-Menten equation using a non-linear regression algorithm such as that described by Marquardt, *J. Soc. Ind. Appl. Math.* 11:431–441(1963).

The deduced amino acid sequence of the recombinant gene for xylose isomerase obtained as described above is shown in FIG. 2 (A and B). This sequence was used in conjunction with x-ray crystallographic analysis and molecular modeling using a computer graphics system to display and analyze three-dimensional structure of the xylose isomerase, including the active site. In this manner the effects of replacement, insertion or deletion of one or more key amino acid residues, for example the effects on noncovalent interactions between the active site and the substrate (glucose) or end product (fructose), are determined. Sites within the DNA sequence for the xylose isomerase of the invention are thus targeted for mutation to improve the activity and stability of the enzyme, for example, to alter the catalytic properties by reducing the $K_S$ and increasing the $k_{catf}$, increasing $K_p$, decreasing $k_{catr}$ and/or by increasing the enzyme's stability toward thermal and chemical inactivation. These same mutations may be used at homologous locations within the DNA sequences for other xylose isomerases obtained from other microorganisms, since many of the amino acid residues selected for mutation are conserved between the various isomerases as shown in FIG. 3.

The present invention promotes high efficiency of glucose conversion and high yields of fructose, using muteins of procaryotic xylose isomerase which may be used industrially for isomerization of glucose to fructose. The various mutation strategies of the present invention may be grouped as follows:

Minimization of Inactivating Chemical Reactions

Mutations are directed to removal of certain amino acids at selected positions that contain an amino group capable of reacting with a reducing sugar such as glucose so as to irreversibly inactivate the enzyme. These mutations result in removal of lysine amino acids, the only amino acid containing epsilon amino groups, that can react with a reducing sugar to irreversibly inactivate the enzyme (i.e., undergo Maillard reaction). In these mutations, as in the others, it is preferable to attempt to maintain similar structure and/or chemical properties, for example by introducing amino acids that have similar numbers of atoms, or by conserving salt bridges, hydrophobic interactions or hydrogen bonds, thereby maintaining a conformation like that of the native protein. In addition, oxidation of methionine, histidine or tryptophan residues at or near the active site may lead to a reduction in catalytic activity. Histidine contains an imidazole group, and tryptophan an indole group that may be oxidized. Mutations are targeted to replace methionine or histidine residues with amino acids that are not likely to be oxidized, such as glutamine or glycine. Arginine contains a guanido group susceptible to modification by dicarbonyl compounds such as 2,3- butanedione, a possible byproduct of the isomerase-catalyzed reaction. Removal or replacement of this amino acid may prevent inactivation.

Enhancement of Catalytic Properties

Based on the x-ray structure of *S. rubiginosus* xylose isomerase, and molecular modeling studies involving substrate docking to the enzyme's active site, tryptophan residues at positions 16 and 137 in the amino acid sequence of the reference enzyme, and a phenylalanine residue at position 94 appear to be critical residues forming the substrate binding site. Because glucose is a larger molecule than xylose (glucose contains an additional —$CH_2OH$), the binding site of xylose isomerase appears to be too small to readily accommodate the larger glucose molecule. Replacement of these key amino acid residues by amino acids possessing small functional groups may reduce the $K_S$ for glucose. $k_{catr}$, $k_{catf}$ and/or $K_P$ may also be altered.

Thermostabilization

Glycine residues in selected positions, e.g. alpha helices, β-strands or random structures that can accept increased bulk of the substituted methyl group, are substituted with alanine residues to introduce stabilization. In addition, proline substitutions are made at selected positions (the polypeptide-backbone torsion angles must accept the atypical proline angle values) to reduce the entropy of the unfolded form of the protein, and stabilize the native conformation. Additional stabilizing alterations include the introduction of disulfide bridges at conformationally acceptable positions in the XI structure. Both intersubunit or intrasubunit disulfide bridges in the tetrameric xylose isomerase are contemplated within this invention. Introduction of aromatic amino acid residues such as tyrosine, phenylalanine and tryptophan near aromatic clusters within the enzyme are also within the scope of the invention, to stabilize the enzyme at sites where the additional bulk of aromatic groups will not distort the overall conformation.

To prevent deamidation reactions, selected amino acids (asparagine and glutamine residues) near interfaces between subunits are altered by substitutions with amino acids such as alanine and valine that cannot undergo such reactions.

In addition, or as an alternative to amino acid substitution for increased stability, the structural gene for xylose isomerase is duplicated and the two copies of the gene are fused via a DNA sequence encoding a short peptide segment, between 3 and 10 amino acids long, between the N-terminus of one gene copy and the C-terminus of the other. Preferably oligoglycine or a combination of glycine and additional amino acids such as alanine, serine, threonine or proline is used as the short peptide sequence.

The mutated isomerase proteins, or "muteins", may be more stable than the currently used naturally occurring enzymes at the high temperatures, near 100° C., needed to reach the desired conversion levels (greater than 55% fructose). Some of the stabilizing mutations simply reduce the rate of thermally induced unfolding of the protein conformation. Others prevent covalent modifications of the enzyme which might reduce catalytic activity or conformational stability. The isomerase muteins may have improved catalytic activity for any combination of three reasons: increased intrinsic catalytic activity, increased affinity for substrate glucose, or decreased affinity for product fructose.

These improvements are not completely independent. For example, increasing affinity for substrate can result in increased thermal stability by reducing the fraction of time that an enzyme active site is empty, as it generally is true that binding of substrates or products to an enzyme active site stabilizes the protein conformation.

The improvements contemplated herein are intended to improve the economics of glucose isomerization for several reasons. Increased stability toward conformational unfolding (thermal stabilization) and/or inactivating covalent modification increases the permissible operating temperature and resulting percent conversion of glucose, or increases the operating lifetime of a given batch of catalyst, thus reducing the cost of catalyst per unit of product. Increased catalytic activity at a given operating temperature allows a given amount of catalyst to bring a mixture of glucose and fructose closer to equilibrium in less time. It also may reduce the amount of enzyme required, again lowering the cost of catalyst per unit of product.

Any number of mutations proposed herein may be combined in a single mutein. Obviously, a particular substitution at one location rules out replacement with another amino acid at that same location in that particular mutein.

The isomerases herein may be obtained as salts. Accordingly, the present invention includes electrically neutral and salt forms of the designated xylose isomerases and the term xylose isomerase refers to the organic structural backbone regardless of ionization state.

The muteins are particularly useful for the food processing industry. The xylose isomerases may be produced by fermentation as described herein and recovered by suitable techniques. (Anstrup, *Industrial Aspects of Biochemistry*, ed. B. Spencer, pp 23-46 (1974)).

The following examples are presented to illustrate the present invention and to assist one of ordinary skill in making and using the same. The examples are not intended in any way to otherwise limit the scope of the disclosure or the protection granted by Letters Patent hereon.

EXAMPLE I

Purification of Xylose Isomerase (XI) from Streptomyces Rubiginosus Strain C3

XI was isolated from *Streptomyces rubiginosis* strain C3 obtained from CETUS Corporation, Emeryville, Calif. using the following method.

The purification scheme for crude extract involves the following steps: filtering the extract to remove insoluble material; precipitating enzyme with alkyldimethylbenzyl ammonium chloride (BTC) to remove impurities not precipitated with the BTC; further filtration with salt; removal of BTC by adsorption resin; desalting and concentration by ultrafiltration to remove low molecular weight impurities; adsorption of the isomerase enzyme on a GDC (granular DEAE cellulose) column to remove unadsorbed impurities; washing and eluting column with sodium chloride (NaCl) to solubilize the isomerase; and gel filtration. Ultrafiltration is used for enzyme desalting and concentration between the various steps and in some cases the preparation may be sufficiently pure for certain applications so that the gel filtration step may be eliminated.

Crude isomerase extract was prepared by fermentation of Streptomyces strain C3 which was derived from ATCC 21,175. At the completion of fermentation, i.e., when isomerase activity was at a maximum, the intracellular enzyme was extracted from the mycelia by treatment with lysozyme and cationic surfactant (BTC). The extraction procedure was rapid and efficient with complete isomerase solubilization occurring within 2-4 hours. After extraction, insoluble materials, consisting mostly of disrupted cell debris, were removed by precoat filtration. The resulting soluble extract had an isomerase potency of 35-50 international xylose isomerase units ("U")/ml. The specific activity (U/mg protein) of the crude extract was difficult to estimate because protein determination is limited by interference from various components of the extract. 2-3 U/mg was expected.

Any turbidity in the crude extract was removed by laboratory filtration through a precoat of filter aid.

The optimum concentration of BTC to be added to the extract was determined in a preliminary experiment. This was accomplished by taking several aliquots of the extract and adding various amounts of BTC. The resulting precipitates were moved by centrifugation and aliquots of the supernates taken for isomerase assay as described below. The lowest BTC concentration at which complete or nearly complete isomerase precipitation takes place was the optimum concentration for the larger scale precipitation with the crude extract. Generally a BTC concentration of 1000-2000 ppm should be sufficient for complete isomerase precipitation.

For BTC precipitation the pH of the extract was adjusted to pH 7.0, 7.3 and the BTC solution (100 mg/ml) added slowly with vigorous stirring. After additions of BTC the suspension was stirred for 20-30 minutes. A small aliquot was taken and centrifuged, and the supernates were assayed for isomerase activity to test for completeness of isomerase precipitation.

When precipitation was complete, filter aid (approximately 5 g HyFlo SuperCAl/liter of suspension) was admixed and the suspension filtered using Whatman 3 paper and a laboratory vacuum. The resulting filter cake was washed with several portions of water to remove entrained solubles.

To solublize the precipitated BTC-isomerase complex, the filter cake was suspended in a minimum volume of 0.5 N NaCl, pH 7.0 (100-200 ml per liter of original extract) and stirred for thirty minutes. The suspension was then filtered using a vacuum and the filter cake washed with several small portions of salt solutions without vacuum. The filtrate and washings were well mixed and samples taken for determination of protein, BTC, and isomerase activity.

Protein Concentration

Protein concentration was determined by measuring ultraviolet absorbance at 280 nm. An Extinction Coefficient of 15.4 (1 mg/ml=1.54 $A_{280}$), determined based on amino acid composition of the protein) was used to convert absorbance to isomerase protein concentration. Samples for protein determination were diluted to an $A_{280}$ of 0.2-1.0. Turbid samples should be filtered or centrifuged before dilution. Absorbance was measured in 1 cm quartz cuvettes using a suitable blank. The absorbance was scanned from approximately 320 nm to approximately 240 nm. Purified isomerase has a characteristic absorbance spectrum with a distinctive maximum at 278 nm and a minimum at 250 nm. An $A_{280}/A_{260}$ ratio of approximately 1.6 was typical of highly purified isomerase preparations.

BTC Estimation

Soluble BTC-835 (alkyldimethylbenzyl ammonium chloride, Onyx Chemical Co.) concentration was estimated by measuring ultraviolet absorbance over the 290-240 nm range. BTC has three distinct absorbance peaks at 269, 262 and 256 nm with very little absorbance at 280 nm. To estimate BTC concentration the absorbance at 262 nm was measured and corrected for protein absorbance at this wavelength. An extinction coefficient of 9.5 was used to convert absorbance to concentration (1 mg/ml=0.95 $A_{262}$).

Ultrafiltration

Depending upon the volume of sample to be handled, ultrafiltration was accomplished with either an Amicon CH4 hollow fiber concentrator or with Amicon 401 or 201 stirred cells using the appropriate Amicon cartridges or membranes. Monitoring for enzyme retention was accomplished by periodic UV scan of the ultrafiltrates. Where enzyme leakage was indicated by UV absorbance, samples were checked by the isomerase described below.

Most of the procedures described were carried out at room temperature. To minimize changes of microbial contamination enzyme solutions were filtered through 0.45 or 0.2 Millipore membranes, and were stored in the cold between purification steps.

BTC removal was effected by treatment with a strong acid cation exchange resin in the sodium form. Resins such as AG-50 (BioRad Laboratories, Richmond, Calif.) will adsorb BTC in the presence of 0.5N NaCl without affecting isomerase. Other procedures for removal of BTC, include treatment with activated carbon or ultrafiltration-diafiltration.

The AG-50 resin was added directly to the BTC-isomerase (approximately 1 g dry base resin per 100 ml) solution and the pH was adjusted to 7.0 after a brief period of gentle stirring. The suspension was stirred gently for about 20 minutes and the pH readjusted to 7 when necessary. The resin was allowed to settle by gravity and a sample of the supernatant was taken for UV scan to test for BTC removal. If BTC removal was not complete, additional resin was added until no BTC remained. An additional test for BTC removal can be carried out by diluting a portion of the resin supernate 1 to 5 with water. The presence of residual BTC will be indicated by the formation of a precipitate due to the insolubility of the BTC-isomerase at lower salt concentration.

After removal of BTC, the resin was removed by filtration, and the filtrate desalted and concentrated by ultrafiltration with an Amicon CH4 hollow fiber cartridge. The starting solution for ultrafiltration was optimally free of any insoluble material, and was filtered through a 0.45 micron filter when necessary. Ultrafiltration was carried out until the retentate volume was reduced to a minimum consistent with reasonable flux rate. The retentate was then diluted with 5-10 volumes of water and the pH readjusted to 7. Ultrafiltration was continued. This dilution-diafiltration was repeated two more times. The final retentate had a specific activity of 30-35 U/ml. Recovery of activity based on the starting crude extract was 85-90%.

To prepare the enzyme for GDC adsorption sufficient 1M Tris buffer, pH 7.0, and 1M $MgSO_4$ was added so that the concentration of each was 10 mM in the enzyme solution. Microbial contamination, when the enzyme was to be stored for any period of time, was reduced by filtration through a 0.45 micron Millipore filter.

GDC adsorption-desorption was carried out with a column of granular DEAE-cellulose (Whatman Ltd., Clifton, N.J.). To prepare the column, 300 g GDC was equilibrated in 10 mM Tris buffer. This suspension was poured into a 5cm×20 cm chromatography column to form a uniform bed. The column was then washed using two liters of 10 mM Tris at a flow rate of approximately 10 ml/min. Washing with buffer was continued until the effluent pH was between 6.8 and 7.2.

The enzyme solution (ultrafilter retentate) was applied directly to the column at a flow rate of approximately 5 ml/min. A total of $2 \times 10^5 - 3 \times 10^5$ U of enzyme can be applied. During enzyme application, and in subsequent washing and elution steps, the effluent from the column was monitored for UV absorbance and periodic samples were assayed using the isomerase assay. After the enzyme was applied, the column was washed with 3-4 liters of 0.15N NaCl at a flow rate of approximately 20 ml/min. This washing step removed weakly adsorbed impurities, as evidenced by the yellow color and UV absorbance of the effluent. Near the end of the washing step the effluent was nearly colorless and contained very little UV absorbing material.

Elution of the isomerase was accomplished by washing the column with 0.45N NaCl in 10 mM Tris, pH 7, at a flow rate of 10 ml/min. The effluent from the elution step was collected in 200 ml fractions which were monitored for UV absorbance and isomerase activity. Isomerase activity began to elute immediately after a void volume of 800-900 ml of eluate was collected. More than 90% of the total activity eluted in the first five 200 ml fractions of eluate. Fractions with isomerase activity of 20 U/ml and specific activity of 40 U/mg were pooled for desalting and concentration by ultrafiltration.

The pooled GDC column fractions were desalted and concentrated using either the CH4 concentrator or the 401 stirred cell (30,000 molecular weight cutoff). The CH4 unit was used to reduce the volume to 200 ml, and two or three 5 volume diafiltrations were conducted with water to remove salt. The CH4 retentate was then further concentrated with the stirred ultrafiltration cell. If the enzyme was to be further purified by gel filtration, diafiltration with 20 mM phosphate buffer, pH 7.0, was used to adjust the buffer concentration.

Recovery of activity from the GDC step was greater than 90% of the activity applied to the column, yielding an overall recovery of about 80% based on the starting extract. The specific activity was 40-45 U/mg, indicating that the enzyme was 90-95% pure on a protein basis.

Gel filtration was carried out with a column of Fractogel TSK HW-55 (Pierce Chemical Co., Rockford, Ill.) capable of separating proteins in the 50,000-500,000 MW range. The gel was equilibrated in 20 mM sodium phosphate buffer according to the manufacturer's recommendation, and used to prepare a 2.5 cm×90 cm uniformly packed bed. The column was then equilibrated with phosphate buffer at a flow rate of 0.6-0.7 ml/min for at least 16 hours before use.

Total sample volume applied to the column was less than 20 ml, with smaller volumes being more desirable. The sample was applied carefully to the top of the column without disturbing the gel bed, and allowed to flow into the column by gravity. Application of the sample was followed by two 1 ml buffer applications to assure that the sample was completely washed into the bed. The column was then eluted with 20 mM phosphate buffer at a flow rate of 0.6-0.7 ml/min. The column effluent was continuously monitored for absorbance at 280 nm, and fractions (10 ml each) were collected automatically. The fractions were analyzed for protein ($A_{280}$) and isomerase activity as described elsewhere.

Typically, for the isomerase purified by BTC precipitation followed by DGC adsorption-desorption, enzyme elution was preceded by elution of a small peak of U.V.-absorbing material which probably represents some higher molecular weight protein contaminant.

The specific activities of the first and last fractions from isomerase elution were generally lower than those of the middle fractions. These first and last fractions were discarded, since enzyme purity was considered to be more important than recovery. The pooled active fractions were ultrafiltered with a 100,000 molecular weight cutoff membrane using the 201 stirred cell. Very little U.V. absorbing material was found in the ultrafiltrate from this step, indicating that the enzyme was free of lower molecular weight protein contaminants. The final diafiltered retentate was filtered through a 0.2 Millipore filter to eliminate microbial contamination during storage.

The final specific activity was 46 U/mg with an overall recovery of about 70% based on starting extract.

The results of each step as set forth above were tabulated in terms of total activity, specific activity, and recovery as shown in Table I.

TABLE I

ISOMERASE PURICIATION

| Procedure | Fraction | Vol. (ml) | Potency (U/ml) | Total Activity (U) | Protein (mg/ml) | Specific Activity (U/mg) | Recovery % of Start |
|---|---|---|---|---|---|---|---|
| BTC-Precipitation | I | 3500 | 103 | $3.59 \cdot 10^5$ | | | 89.2 |
| UF YM 30 | II | 2000 | 179 | $3.48 \cdot 10^5$ | 5.70 | 31.2 | 86.4 |
| GDC Column (2 batches) | III | 2400 | 137 | $3.29 \cdot 10^5$ | 3.21 | 42.7 | 81.6 |
| UF YM 30 | IV | 200 | 1565 | $3.13 \cdot 10^5$ | 35.9 | 43.6 | 77.6 |
| Gel Filtration[1] | V | 90 | 252 | $2.27 \cdot 10^4$ | 5.5 | 45.9 | 70.5[1] |
| UF XM-100 | VI | 25 | 904 | $2.26 \cdot 10^4$ | 19.7 | 46.0 | 70.2[1] |

[1] $2.5 \cdot 10^4$ U of Fraction IV was used for gel filtration step.

Alternatively XI protein is isolated from *Streptomyces rubiginosus* strain C3 derived from *S. rubiginosus* ATCC 21,175 using the method described in U.S. Pat. No. 4,410,627, which is incorporated herein by reference. The strain is grown by submerged aerobic fermentation on a medium with the following composition (by percent weight) dextrose 9.0%, corn steep liquor (solids) 0.06%, diammonium phosphate 0.008%, magnesium sulfate 0.06%, antifoam (pluronic PL-61) 0.003%. The medium is sterilized at 121° C. for 45 min, cooled and adjusted to pH 5 6.8-7.0. The medium is inoculated with 14% (v/v) of an inoculm comprising the contents of a seed fermenter prepared with the *S. rubiginosus* strain. XI protein is extracted from the *S. rubiginosus* strain by adding 0.35% Maquat MC 1412 (Mason Chemical Co.) and 10 ppm of hen's egg lysozyme and agitating for 5 hr at 40° C., pH 6.3 to 6.6. The mixture is then filtered to provide a solution of unpurified xylose isomerase. The crude isomerase is purified by adsorption on DEAE-cellulose, filtering and washing the adsorbed product with 0.1M NaCl solution to remove impurities, and then desorbing by contacting with 0.45M NaCl solution. The pH of all solutions is maintained at 7.5 during the purification step. The solution of partially purified isomerase obtained thereby is mixed with 3 volumes of 95% ethanol at 0° C. to precipitate the isomerase. Perlite filter aid is added, the solids recovered by filtration, and air dried to provide a soluble XI preparation containing 2500 U/g. Specific activity of the preparation thus prepared is 40 U/mg of protein.

Purification following these procedures results in an enzyme having greater than 90% purity based on SDS-PAGE electrophoresis.

Protein Concentration

Protein concentration was determined by measuring ultraviolet absorbance at 280 nm. An extinction coefficient of 15.4 (1 mg/ml=1.54 $A_{280}$) was determined, based on the amino acid composition of the protein, and used to convert absorbance to isomerase protein concentration. Samples for protein determination were diluted to an $A_{280}$ of 0.2–1.0. Turbid samples should be filtered or centrifuged before dilution. Absorbance was measured in 1 cm quartz cuvettes using a suitable blank. The absorbance was scanned from approximately 320 nm to approximately 240 nm. Purified isomerase has a characteristic absorbance spectrum with a distinctive maximum at 278 nm and a minimum at 250 nm. An $A_{280}/A_{260}$ ratio of approximately 1.6 was typical of highly purified isomerase preparations.

Xylose Isomerase Assay

Xylose isomerase activity was measured by incubating the protein sample with a buffered solution of glucose for a fixed period of time, quenching the reaction, and then quantitating the amount of product (fructose) made by high performance liquid chromatography (HPLC) analysis.

1 unit of activity is that amount of enzyme that produces 1 µmole fructose/min under the defined reaction conditions.

A 20 µl sample of enzyme (0–3 units of activity) was mixed with 1 ml of substrate mixture (3M in D-glucose, 25 mM maleic acid (adjusted to pH 6.5 at 60° C. with NaOH), 10 mM $MgSO_4$ and 1 mM $CoCl_2$) (previously equilibrated at 60° C.) to initiate the reaction:

The enzyme plus substrate mixture was incubated for 20 minutes at 60° C. in a closed tube. At the end of this incubation, 0.5 ml of 1N HCl was added to stop the reaction. Precipitated protein was removed by centrifugation, and an aliquot of the supernatant solution was removed for quantitation of fructose by HPLC analysis.

The separation of fructose from unreacted glucose was accomplished using a Beckman liquid chromatograph equipped with a Waters Assoc. (Waters Assoc., Milford, Mass.), WISP 710B autoinjector, Waters Assoc. differential refractometer (Model R401) and a Shimadzu C-R3A integrator (Shimadzu Corp., Kyota, Japan). Carbohydrates were separated using an Applied Science carbohydrate analysis column (amine phase, 250 mm×4.6 mm) using isocratic sample elution with an acetronitrile/water (80%/20%) solvent flowing at 1.3 ml/min. Integration of peak areas for the resolved fructose peaks from standard fructose solutions or from test samples, allowed quantitation of fructose production for the test samples during the 20 minute incubation.

EXAMPLE II

N-terminal Sequencing of *S. rubiginosus* Xylose Isomerase

Purified XI is subjected to further analysis to determine the amino ("$NH_2$")-terminal end of the mature protein.

Edman degradation determination of XI amino acid sequence

Sequence analysis by automated Edman degradation was performed using a Beckman Model 890C sequencer (Beckman Instruments, Palo Alto, Calif.) following standard methodology. In some instances, in order to reduce background and improve signal to noise ratio, orthopthalaldehyde was used to block proline residues according to the method of Bauer et al., *Anal. Biochem.* 137:134 (1984), incorporated by reference herein. Results for the first 20 residues of the amino-terminal sequence obtained for XI are shown in Table II.

TABLE II

| | C-3 Xylose Isomerase Amino Acid/Yield (nmol) | | | |
|---|---|---|---|---|
| Cycle No. | Major Sequence | | Minor Sequence | |
| 1 | Met | 10.47 | — | |
| 2 | Asn | 10.44 | Met | 0.84 |
| 3 | Tyr | 10.21 | Asn | 2.73 |
| 4 | Gln | 11.23 | Tyr | 1.70 |
| 5 | Pro | 6.78 | Gln | 4.07 |
| 6 | Thr | 2.11 | Pro | 1.78 |
| 7 | Pro | 5.88 | Thr | 0.77 |
| 8 | Glu | 9.79 | Pro | 2.56 |
| 9 | Asp | 7.83 | Glu | 3.74 |
| 10 | Arg | 5.37 | Asp | 3.43 |
| 11 | Phe | 9.26 | Arg | 3.23 |
| 12 | Thr | 2.14 | Phe | 4.39 |
| 13 | Phe | 8.68 | Thr | 0.91 |
| 14 | Gly | 7.03 | Phe | 4.45 |
| 15 | Leu | 10.09 | Gly | 3.45 |
| 16 | Trp | 4.25 | Leu | 6.25 |
| 17 | Thr | 5.67 | Trp | 1.37 |
| 18 | Val | 8.52 | Thr | 1.32 |
| 19 | Gly | 5.87 | Val | 4.76 |
| 20 | Trp | 5.01 | Gly | 3.96 |

EXAMPLE III

Construction of oligodeoxynucleotide probes for detection of the N-terminal region of XI from strain C3

Oligodeoxynucleotide probes were made using conventional methods. Using polynucleotide kinase, the probes were labeled with [32γP]-ATP having a specific activity of 3000 Ci/mole, supplied by New England Nuclear Labs (Boston, Mass.). The labeled probes were purified by gel filtration on a Biogel P-4 gel (BioRad Laboratories, Richmond, Calif.). Two pools of four probes were made. Pool 1 consisted of probes having the following sequences GGTTG(A/G)TA(A/G)TT-CAT and pool 2 consisted of probes having the following sequences GGCTG(A/G)TA(A/G)TTCAT, wherein the nucleotides in the parentheses are alternate nucleotide bases. The two pools were constructed to cover all possible nucleotide ambiguities in the XI gene in the region coding for the $NH_2$-terminal region.

EXAMPLE IV

Cloning of the XI gene of strain C3 in Plasmid pBR322

Plasmid preparation

Plasmid pBR322 DNA was isolated and purified essentially as described in Birnboim et al., *Nuc. Acids Res.* 7:1513(1979), incorporated by reference herein. After purification of the plasmid in CsCl, the DNA preparation was further digested with RNase at a concentration of 40 µg/ml at 37° C. for 30 minutes and subsequently extracted with phenol and ether. The RNA-free plasmid DNA was then completely digested with Bam HI and dephosphorylated with calf intestinal alkaline phosphatase.

Preparation of *S. rubiginosus* Strain C3 DNA

High molecular weight chromosomal DNA for *S. rubiginosus* strain C3, a derivative of ATCC 21,175, was isolated according to the methods of Chater et al., *Cur-* rent *Topics in Microbiology and Immunology* 96:69 (1982), incorporated by reference herein. The DNA was then partially digested with restriction enzyme Sau 3AI (New England Biolabs, Beverly, Mass.) under the conditions suggested by the manufacturer. The 4 to 8 kb fragments from the partially digested chromosomal DNA were isolated by sucrose density gradient centrifugation and were concentrated by DEAE ion exchange chromotography.

Ligation of *S. rubiginosus* DNA into pBR322 to form a gene bank and Transformation of *E. coli* with the resulting vector Two hundred µg of the Bam HI digested cloning vector (pBR322) were mixed at a 1:2 molar ratio with the partially digested *S. rubiginosus* DNA in ligation buffer under sticky end conditions. After ligation, an aliquot of the reaction mixture containing approximately 100 µg of the cloning vector was used to transform CaCl$_2$-treated competent *E. coli* strain MM294. The transformed *E. coli* were diluted ten-fold with 2×L-broth by volume and were incubated for 90 min at 37° C. The culture was then further diluted 25-fold with 2×L-broth containing 100 µg/ml ampicillin The dilute culture was then incubated at 37° C. with shaking, overnight. After incubation, the concentration of glycerol in the culture was adjusted to 15% and the mixture was stored at 70° C.

Identification of xylose isomerase clones

The transformant gene bank prepared as described above was thawed and plated on L-agar plates containing 40 µg/ml of ampicillin to obtain approximately 400 individual colonies per plate. Colonies were then transferred to nitrocellulose filters as described in Maniatis et al., *Molecular Cloning*, supra. Filters were prehybridized by the method described in Woo, *Methods in Enzymology* 68:389 (1979), incorporated by reference herein. Processed filters were then hybridized with [$^{32}\gamma$P]-labeled oligonucleotide pool 2(10$^6$ cpm/filter) in hybridization buffer (5XSSC, 5X Denhardt's solution, 50 mM sodium phosphate pH 7.0, 100 µg/ml sheared calf thymus DNA, and 1% SDS) at 35° C. overnight. Filters were subsequently washed with 5XSSC, 2XSSC, 2XSSC and 1XSSC containing 0.1% SDS at hybridization temperature (35° C.) for 15 min. each.

Fifty percent of the transformants were both ampicillin and tetracycline resistant indicating that about half of the transformants carried inserted *S. rubiginosus* DNA. To confirm this conclusion, ten ampicillin resistant transformants were randomly picked, the plasmid DNA extracted and purified, and restriction enzyme analysis with Eco RI was carried out. Agarose gel electophoresis of the digested plasmid DNA showed that 50% of the DNA was about 4 to 8 kb larger than pBR322. Based on these results, approximately 20,000 transformants were obtained using 20 µg of the cloning vector. Based on the reported size of the Streptomyces genome, a complete gene library of *S. rubiginosus* was obtained. Of 20,000 colonies screened, 15 colonies hybridized to the mixture of oligonucleotides in pool 2.

The plasmids of each positive colony were isolated as described above and characterized by restriction enzyme fragment analysis using Pst I, Bgl III and Sma I. Three types of clones were distinguished. Two of the representative clones, pTW1 and pTW2, carried 4.3 and 7.5 kb Sau 3Al inserts, respectively. The third representative clone, pTW3, carried a 12 kb insert which was believed to arise by linkage of two Sau 3Al fragments of the *S. rubiginosus* digest.

Of the pool 2 primers, the oligodeoxyribonucleotide designated CS26 having the sequence 5'-GGCTGGTAGTTCAT-3', was found to hybridize strongly with the *S. rubiginosus* C3 DNA, and in particular, hybridized 10 times more strongly with the transformant designated pTW1 which carried a 4.3 kb insert. An oligonucleotide complementary to C26, designated HW03, was constructed for further use.

Plasmids pTW1, pTW2 and pTW3 were analysed with a number of restriction enzymes. The 1.35 kb Sal I, 2.3 kb Pst I and 1.8 kb Sma I restriction fragments from the plasmid inserts hybridized with probe CS26. *S. rubiginosus* genomic DNA was digested with the same restriction endonucleases, and fragments of the proper molecular weight hybridized under stringent conditions with CS26, confirming the location of the translation start site of the gene. To determine the translational and transcriptional orientation of the gene, the Nru I-Pst I restriction fragment carrying the 5' end of the gene was further subcloned into the Sma I-Pst I sites of either M13mp10 or M13mp11 replicative form (RF) DNA (obtained from Bethesda Research Laboratories, Bethesda, Md). Single-stranded DNA was isolated, purified as described in Messing, *Methods in Enzymology*. 101:20 (1983), incorporated by reference herein, and hybridized to probes CS26 and HW03. The results shown in Table III indicated that the transcriptional direction of the gene is from left to right in the restriction map of the gene shown in FIG. 1.

TABLE III

Hybridization of Oligodeoxyribonucleotide probes CS26 and HW03 with the Single-Stranded Recombinant Phage DNAs carrying the 5'-end of the Glucose Isomerase Gene in Two Different Orientations

| Insert SS Phage DNA | Cloning Orientation[1] | Sites | Hybridization[2] CS26 | HW03 |
|---|---|---|---|---|
| M13mp10 | − | (5')-SmaI-PstI | − | − |
| M13mp11 | − | (5')-PstI-SmaI | − | − |

[1] ( − ) orientation indicates that the sense-strand of the insert is in the phage.
( − ) indicates that the antisense-strand is in the phage.
[2] one µg of single-stranded phage DNA was used for each hybridization

EXAMPLE V

Sequencing of the xylose isomerase gene

The DNA sequence of the entire xylose isomerase gene was determined based upon the restriction map of FIG. 1 and the determination of the transcription orientation. The complete DNA sequence and deduced amino acid sequence is shown in FIG. 2. Comparison of the entire sequence for *S. rubiginosus* XI with published sequences for other known native procaryotic isomerases (FIG. 3) reveals substantial sequence identity between the XI of these organisms.

For the xylose isomerases with limited amino acid sequence identity to *S. rubiginosus* xylose isomerase, (i.e. less than 50%), for example enzyme obtained from *E. coli* and *B. subtilis*, the conserved amino acid residues are primarily those located at or near the active site of the enzyme. It is contemplated that the below-described alterations in amino acids at the active site of *S. rubiginosus* XI are likely to produce muteins of these enzymes with similar characteristics to the XI muteins resulting from similar changes in *S. rubiginosus* XI. In enzymes that are more closely homologous to *S. rubiginosus* XI, such as *Ampullariella sp.*, similar alterations in amino acid residues located in other regions of the protein, as well as in the active site, are likely to result in comparable changes in the stability and activity of these enzymes.

EXAMPLE VI

Expression of Xylose Isomerase Muteins

Construction of the Expression Vector

Construction of an expression vector plasmid pTW11 for expression of the XI muteins in *E. coli* was as follows. The 1.4 kb Nru I-Sma I restriction fragment carrying the entire coding sequence of the glucose isomerase gene from pTW1 was isolated and subcloned into the Sma I site of M13mp10 RF DNA. The orientation was such that the ATG initiation codon of the gene was approximately 220 bp from the Eco RI site of the phage, which was designated phage φTW23. Ligation of the XI DNA sequence into the phage destroyed the translation termination codon of the gene, and a new one was created by site-specific mutagenesis as described in Zoller and Smith, *Methods in Enzymology* 100:468 (1983), incorporated by reference herein, using a synthetic oligodeoxyribonucleotide with the sequence 5'-CGACTCTAGATCATCCCCGGGCG-3'. The new phage having the desired insert was screened by hybridization with the mutagenesis primer labeled using polynucleotide kinase and [32γP]ATP (3000 Ci/mmole, New England Nuclear) as follows: prehybridization was carried out by the procedure of Woo, *Methods in Enzymology* 68:389 (1979), incorporated by reference herein. Processed filters were then hybridized with the [32P]—labeled oligodeoxyribonucleotide ($10^6$ cpm/filter) in 20 ml hybridization buffer (5XSSC, 5×Denhardt's solution, 50 mM sodium phosphate, pH 7.0, 100 μg/ml sheared calf thymus DNA, 1.0% SDS) at 68° C., overnight. Filters were subsequently washed (15 min each) with 5XSSC, 2XSSC and 1XSSC containing 0.1% SDS at hybridization temperature (68° C.). The phage having the proper sequence, designated phage TW31, was confirmed by sequencing.

The same procedure was used to insert a Hind III site preceding the translation initiation codon of the xylose isomerase gene in phage φTW31 except that the synthetic oligodeoxyribonucleotide had the sequence 5'-GTACTTCATAACTCTTCGCGGCTC-3' and the hybridization and washes were carried out at 65° C. The phage carrying the xylose isomerase gene with the introduced translation termination codon and two Hind III sites bordering the gene was designated phage φTW32. The xylose isomerase gene was isolated from phaqe φTW32 by digestion with Hind III and was ligated into the Hind III site of *E. coli* expression vector pTRP3 (ATCC No. 39,946 deposited Dec. 18, 1984, described by Goeddel et al. *Nuc. Acids. Res.* 8:4052 (1980)), incorporated by reference herein. The resulting plasmid having the expression of xylose isomerase under the control of the trp operon promotor and trpE translation initiation signal, was designated pTW11. The plasmid having the xylose isomerase gene in the opposite orientation was designated pTW12.

Preparation of *E. coli* Strain Lacking XI for Screening

The *E. coli* strain DG101 (thi-1, endA1, hsdR17, SupE44, lac18, lacZM15) was mutagenized using Nitrosoguanidine (NTG) at a concentration of approximately 200 μg/ml of medium for approximately 30 minutes. The bacteria were pelleted, washed in minimum salts medium, resuspended in minimal salts medium containing 0.5% xylose, and were grown for approximately 30 minutes at 37° C. D-cycloserine was added to a concentration of 100 μg/ml and the culture was incubated at 37° C. for approximately 30 minutes. The cells were centrifuged, washed in minimal salts medium, and then grown in rich L-broth for approximately 30 minutes at 37° C. The culture was plated on McConkey medium containing 1% xylose, and white colonies were selected. White colonies were transformed with plasmid pTW11 plated on MacConkey medium without xylose. Red colonies, in which the absence of xylose isomerase was complemented by the plasmid, were picked. *E. coli* strain DG101 xyl- transformed with pTW11 were deposited into applicants' depository under accession number CMCC 2210. This strain was deposited in the ATCC on Aug. 5, 1987 under accession number 67,489.

Recovery of XI Muteins

The transformed *E. coli* are cultured in LB media with limiting concentrations of tryptophan. After the mutein is induced enzymatically active xylose isomerase mutein is recovered essentially as described in Example I and in U.S. Pat. No. 4,410,627, incorporated by reference herein.

EXAMPLE VII

Site-Specific Mutagenesis of the *S. rubiginosus* xylose isomerase gene to Minimize Inactivating Reactions The specific locations for alteration of the DNA sequence encoding XI were selected based on computer-assisted analyses (PS 340, Evans and Sutherland, Salt Lake City, Utah, using MOGLI and Proteus software) of the x-ray crystal structure of xylose isomerase obtained by standard x-ray crystallography methodology.

Oligonucleotide primers, as described below, are synthesized complementary to the DNA sequence of the reference xylose isomerase gene fragment, except for regions of limited nucleotide mismatching to accomplish the desired mutation. Gapped circle site-specific mutagenesis as described by Kramer et al., supra, is used to convert the amino acid at the selected position to a different amino acid. Towards this end, plasmid pTW11 and phage ml3mpl0 carrying amber mutations are digested completely with Eco RI and Bam HI. The small fragment of pTW11 and the large fragment of M13mp10 are isolated and ligated together. The phage having the small Eco RI- Bam HI fragment from pTW11 and large fragment of M13mp10 is designated TVW8. To form the gapped circle DNA for use as a template for the oligonucleotide-directed mutagenesis single-stranded TVW8 DNA is mixed with Eco RI- Bam HI digested M13mp19 RF DNA and the two DNAs are melted together at 100° C. and reannealed at 67° C. for 30 minutes. A "gapped circle" in which the DNA sequence to be mutagenized remains single-stranded and the remaining DNA is double-stranded is formed in which the single-stranded region includes the XI gene.

The oligonucleotide primers described below are hybridized to the gapped circle DNA (phage TVW8) under hybridization conditions, for example, in a mixture containing 100 mM NaCl, 20 mM Tris-HCl, pH 7.9, 20 mM MgCl2 and 20 mM β-mercaptoethanol by heating at 67° C. for five minutes and 42° C. for 25 minutes. Primer extension is carried out using DNA polymerase large fragments in the presence of dNTPs. The ends of the extended primer are ligated using T4 ligase and ATP. The reactions are terminated by heating to 80° C. The mixture is then used to transform competent E. coli strain HB 2151, which are plated onto agar plates and incubated overnight to obtain phage plaques, and grown under conditions suitable for inducing the phage. The plaques are probed using the same [32γP]-labeled primer using kinase at standard prehybridization and hybridization conditions at high stringency (e.g. 42° C. for 8 hours). Plaques which hybridize to probes are lifted and are confirmed by sequencing. The phage DNA containing the coding sequence for the mutagenized xylose isomerase gene are isolated. The DNA segment comprising the mutagenized XI gene is removed by Hind III digestion. The small Hind III fragment is isolated, purified, and ligated into plasmid pTRP3, previously digested with Hind III.

To produce XI genes containing more than one modification, successive rounds of mutagenesis, each using the appropriate primer, are carried out.

Mutein-Encoding primer Sequences

The following oligonucleotide primers are used for sitespecific mutagenesis to obtain muteins of xylose isomerase resistant to chemical inactivation in E. coli:

to convert $Lys_{289}$ to $Arg_{289}$ to obtain the $Arg_{289}XI$ mutein, 5'-CGGTCCGCGGCGGGCGGAAGT-CGAAGTGC-3;

to convert $Lys_{289}$ to $Gln_{289}$ to obtain the $Gln_{289}XI$ mutein, 5'-CGGTCCGCGGCGGCTGGAAGT-CGAAGTGC-3';

to convert $Lys_{289}$ to $Asn_{289}$ to obtain the $Asn_{289}XI$ mutein, 5'-CGGTCCGCGGCGGGTTGAAGT-CGAAGTGC-3';

to convert $Lys_{289}$ to $Asp_{289}$ to obtain the $Asp_{289}XI$ mutein, 5'-CGGTCCGCGGCGGGTCGAAGT-CGAAGTGC-3"

to convert $Lys_{289}$ to $Glu_{289}$ to obtain the $Glu_{289}XI$ mutein, 5'-CGGTCCGCGGCGGCTCGAAGT-CGAAGTGC-3';

to convert $Lys_{289}$ to $Ser_{289}$ to obtain the $Ser_{289}XI$ mutein, 5'-CGGTCCGCGGCGGGGAGAAGT-CGAAGTGC-3';

to convert $Lys_{289}$ to $Thr_{289}$ to obtain the $Thr_{289}XI$ mutein, 5'-CGGTCCGCGGCGGGGTGAAGT-CGAAGTGC-3';

to convert $Lys_{289}$ to $His_{289}$ to obtain the $His_{289}XI$ mutein, 5,-CGGTCCGCGGCGGGTGGAAGT-CGAAGTGC-3';

to convert $Lys_{289}$ to $Tyr_{289}$ to obtain the $Tyr_{289}XI$ mutein, 5'-CGGTCCGCGGCGGGTAGAAGT-CGAAGTGC-3';

to convert $Lys_{289}$ to $Ala_{289}$ to obtain the $Ala_{289}XI$ mutein, 5'-CGGTCCGCGGCGGGGCGAAGT-CGAAGTGC-3';

to convert $Lys_{289}$ to $Val_{289}$ to obtain the $Val_{289}XI$ mutein, 5'CGGTCCGCGGCGGGACGAAGT-CGAAGTGC-3';

to convert $Lys_{289}$ to $Leu_{289}$ to obtain the $Leu_{289}XI$ mutein, 5'-CGGTCCGCGGCGGGAGGAAGT-CGAAGTGC-3';

to convert $Lys_{289}$ to $Ile_{289}$ to obtain the $Ile_{289}XI$ mutein, 5'-CGGTCCGCGGCGGGATGAAGT-CGAAGTGC-3';

to convert $Lys_{183}$ to $Arg_{183}$ to obtain the $Arg_{183}XI$ mutein, 5'-GCGGCTCGTTCGGGCGGGGCTCGATGGC-3';

to convert $Lys_{183}$ to $Gln_{183}$ to obtain the $Gln_{183}XI$ mutein, 5'-GCGGCTCGTTCGGCTGGGGCTCGATGGC-3';

to convert $Lys_{183}$ to $Asn_{183}$ to obtain the $Asn_{183}XI$ mutein, 5'-GCGGCTCGTTCGGGTTGGGCTCGATGGC-3';

to convert $Lys_{183}$ to $Asp_{183}$ to obtain the $Asp_{183}XI$ mutein, 5'-GCGGCTCGTTCGGGTCGGGCTCGATGGC-3';

to convert $Lys_{183}$ to $Glu_{183}$ to obtain the $Glu_{183}XI$ mutein, 5'-GCGGCTCGTTCGGCTCGGGCTCGATGGC-3';

to convert $Lys_{183}$ to $Ser_{183}$ to obtain the $Ser_{183}XI$ mutein, 5'-GCGGCTCGTTCGGGGAGGGCT-CGATGGC-3';

to convert $Lys_{183}$ to $Thr_{183}$ to obtain the $Thr_{183}XI$ mutein, 5'-GCGGCTCGTTCGGGGTGGGCTCGATGGC-3';

to convert $Lys_{183}$ to $His_{183}$ to obtain the $His_{183}XI$ mutein, 5'-GCGGCTCGTTCGGGTGGGGCTCGATGGC-3';

to convert $Lys_{183}$ to $Tyr_{183}$ to obtain the $Try_{183}XI$ mutein, 5'-GCGGCTCGTTCGGGTAGGGCT-CGATGGC-3';

to convert $Lys_{183}$ to $Ala_{183}$ to obtain the $Ala_{183}XI$ mutein, 5=-GCGGCTCGTTCGGGGCGGGCTCGATGGC-3';

to convert $Lys_{183}$ to $Val_{183}$ to obtain the $Val_{183}XI$ mutein, 5'-GCGGCTCGTTCGGGACGGGCT-CGATGGC-3';

to convert $Lys_{183}$ to $Leu_{183}$ to obtain the $Leu_{183}XI$ mutein, 5'-GCGGCTCGTTCGGGAGGGGCT-CGATGGC-3';

to convert $Lys_{183}$ to $Ile_{183}$ to obtain the $Ile_{183}XI$ mutein, 5'-GCGGCTCGTTCGGGATGGCT-CGATGGC-3';

to convert $His_{54}$ to $Gln_{54}$ to obtain the $Gln_{54}XI$ mutein, 5'-GAGGTCGTCGTCCTGGAACGTGACGCC-3';

to convert $His_{54}$ to $Glu_{54}$ to obtain the $Glu_{54}XI$ mutein, 5'-GAGGTCGTCGTCCTCGAACGTGACGCC-3';

to convert $His_{54}$ to $Asn_{54}$ to obtain the $Asn_{54}XI$ mutein, 5'-GAGGTCGTCGTCGTTGAACGTGACGCC-3';

to convert $His_{54}$ to $Asp_{54}$ to obtain the $Asp_{54}XI$ mutein, 5'-GAGGTCGTCGTCGTCGAACGTGACGCC-3';

to convert $His_{54}$ to $Ser_{54}$ to obtain the $Ser_{54}XI$ mutein. 5'-GAGGTCGTCGTCGGAGAACGTGACGCC-3';

to convert $His_{54}$ to $Thr_{54}$ to obtain the $Thr_{54}XI$ mutein, 5'-GAGGTCGTCGTCGGTGAACGTGACGCC-3';

to convert $His_{54}$ to $Ala_{54}$ to obtain the $Ala_{54}XI$ mutein, 5'-GAGGTCGTCGTCGGCGAACGTGACGCC-3';

to convert $His_{54}$ to $Val_{54}$ to obtain the $Val_{54}XI$ mutein, 5'-GAGGTCGTCGTCGACGAACGTGACGCC-3';

to convert $His_{54}$ to $Tyr_{54}$ to obtain the $Tyr_{54}XI$ mutein, 5'GAGGTCGTCGTCGTAGAACGTGACGCC-3';

to convert $His_{220}$ to $Gln_{220}$ to obtain the $Gln_{220}XI$ mutein, 5'GGCCATCTGCTCCTGGCCGACCTCGGG-3';

to convert $His_{220}$ to $Glu_{220}$ to obtain the $Glu_{220}XI$ mutein, 5'-GGCCATCTGCTCCTCGCCGACCTCGGG-3';

to convert $His_{220}$ to $Asn_{220}$ to obtain the $Asn_{220}XI$ mutein, 5'-GGCCATCTGCTCGTTGCCGACCTCGGG-3';

to convert $His_{220}$ to $Asp_{220}$ to obtain the $Asp_{220}XI$ mutein, 5'-GGCCATCTGCTCGTCGCCGACCTCGGG-3'; 'to convert $His_{220}$ to $Ser_{220}$ to obtain the $Ser_{220}XI$ mutein, 5'-GGCCATCTGCTCGGAGCCGACCTCGGG-3';

to convert $His_{220}$ to $Thr_{220}$ to obtain the $Thr_{220}XI$ mutein, 5'-GGCCATCTGCTCGGTGCCGACCTCGGG-3';

to convert $His_{220}$ to $Ala_{220}$ to obtain the $Ala_{220}XI$ mutein, 5'-GGCCATCTGCTCGGCGCCGACCTCGGG-3';

to convert $His_{220}$ to $Val_{220}$ to obtain the $Val_{220}XI$ mutein, 5'-GGCCATCTGCTCGACGCCGACCTCGGG-3';

to convert $His_{220}$ to $Tyr_{220}$ to obtain the $Tyr_{220}XI$ mutein, 5'-GGCCATCTGCTCGTAGCCGACCTCGGG-3';

to convert $Met_{223}$ to $Gly_{223}$ to obtain the $Gly_{223}XI$ mutein, 5'-GTTCAGCCCGGCCCCTGCTCGTGGCC;

to convert $Met_{223}$ to $Ala_{223}$ to obtain the $Ala_{223}XI$ mutein, 5'-GTTCAGCCCGGCCGCCTGCTCGTGGCC;

to convert $Met_{223}$ to $Val_{223}$ to obtain the $Val_{223}XI$ mutein, 5'-GTTCAGCCCGGCCACCTGCTCGTGGCC;

to convert $Met_{223}$ to $Leu_{223}$ to obtain the $Leu_{223}XI$ mutein, 5'-GTTCAGCCCGGCCAGCTGCTCGTGGCC;

to convert $Met_{223}$ to $Ile_{223}$ to obtain the $Ile_{223}XI$ mutein, 5'-GTTCAGCCCGGCGATCTGCTCGTGGCC;

to convert $Met_{223}$ to $Phe_{223}$ to obtain the $Phe_{223}XI$ mutein, 5'-GTTCAGCCCGGCGAACTGCTCGTGGCC;

to convert $Met_{223}$ to $Tyr_{223}$ to obtain the $Tyr_{223}XI$ mutein, 5'-GTTCAGCCCGGCGTACTGCTCGTGGCC;

to convert $Met_{223}$ to $Gln_{223}$ to obtain the $Gln_{223}XI$ mutein, 5'-GTTCAGCCCGGCCTGCTGCTCGTGGCC;

to convert $Met_{223}$ to $Asn_{223}$ to obtain the $Asn_{223}XI$ mutein, 5'-GTTCAGCCCGGCGTTCTGCTCGTGGCC;

convert $Arg_{140}$ to $Gln_{140}$ to obtain the $Gln_{140}XI$ mutein, 5'-CTCGGCACCCTCCTGGCCGCCCAGGC-3';

to convert $Arg_{140}$ to $Asn_{140}$ to obtain the $Asn_{140}XI$ mutein, 5'-CTCGGCACCCTCGTTGCCGCCCCAGGC-3';

to convert $Arg_{140}$ to $Glu_{140}$ to obtain the $Glu_{140}XI$ Mutein, 5'-CTCGGCACCCTCCTCGCCGCCCAGGC-3';

to convert $Arg_{140}$ to $Asp_{140}$ to obtain the $Asp_{140}XI$ mutein, 5'-CTCGGCACCCTCGTCGCCGCCCAGGC-3';

to convert $Arg_{140}$ to $Ile_{140}$ to obtain the $Ile_{140}XI$ mutein, 5'-CTCGGCACCCTCGATGCCGCCCCAGGC-3';

to convert $Arg_{140}$ to $Leu_{140}$ to obtain the $Leu_{140}XI$ mutein, 5'-CTCGGCACCCTCGAGGCCGCCCCAGGC-3';

to convert $Arg_{140}$ to $Ala_{140}$ to obtain the $Ala_{140}XI$ mutein, 5,-CTCGGCACCCTCGGCGCCGCCCCAGGC-3';

to convert $Arg_{140}$ to $Val_{140}$ to obtain the $Val_{140}XI$ mutein, 5'-CTCGGCACCCTCGACGCCGCCCCAGGC-3'; and/or to convert $Arg_{140}$ to $Tyr_{140}$ to obtain the $Tyr_{140}XI$ mutein, 5'-CTCGGCACCCTCGTAGCCGCCCCAGGC-3'

EXAMPLE VIII

Site-Specific Mutagenesis of the Xylose Isomerase Gene to produce Muteins Having Altered Catalytic Properties The procedure of Example VII is followed in substantial detail to produce xylose isomerase muteins having altered catalytic properties. Second strand synthesis and recovery of the desired XI muteins uses the following oligonucleotide primers:

to convert $Trp_{16}$ to $Asn_{16}$ to obtain the $Asn_{16}XI$ mutein. 5'-CCAGCCGACGGTGTTCAGTCCGAAGGTG-3';

to convert $Trp_{16}$ to $Gln_{16}$ to obtain the $Gln_{16}XI$ mutein. 5'-CCAGCCGACGGTCTGCAGTCCGAAGGTG-3';

to convert $Trp_{16}$ to $Ser_{16}$ to obtain the $Ser_{16}XI$ mutein. 5'-CCAGCCGACGGTCGACAGTCCGAAGGTG-3';

to convert $Trp_{16}$ to $Thr_{16}$ to obtain the $Thr_{16}XI$ mutein, 5'-CCAGCCGACGGTCGTCAGTCCGAAGGTG-3';

to convert $Trp_{16}$ to $Gly_{16}$ to obtain the $Gly_{16}XI$ mutein. 5'-CCAGCCGACGGTCCCCAGTCCGAAGGTG-3';

to convert $Trp_{16}$ to $Ala_{16}$ to obtain the $Ala_{16}XI$ mutein. 5'-CCAGCCGACGGTCGCCAGTCCGAAGGTG-3';

to convert $Trp_{16}$ to $Val_{16}$ to obtain the $Val_{16}XI$ mutein, 5'-CCAGCCGACGGTCACCAGTCCGAAGGTG-3';

to convert $Trp_{16}$ to $Leu_{16}$ to obtain the $Leu_{16}XI$ mutein, 5'-CCAGCCGACGGTCAGCAGTCCGAAGGTG-3';

to convert $Trp_{16}$ to $Ile_{16}$ to obtain the $Ile_{16}XI$ mutein, 5'-CCAGCCGACGGTGATCAGTCCGAAGGTG-3';

to convert $Trp_{16}$ to $Tyr_{16}$ to obtain the $Tyr_{16}XI$ mutein, 5'-CCAGCCGACGGTGTACAGTCCGAAGGTG-3';

to convert $Trp_{16}$ to $Phe_{16}$ to obtain the $Phe_{16}XI$ mutein. 5'-CCAGCCGACGGTGAACAGTCCGAAGGTG-3';

to convert $Trp_{16}$ to $His_{16}$ to obtain the $His_{16}XI$ mutein. 5'-CCAGCCGACGGTGTGCAGTCCGAAGGTG-3';

to convert $Trp_{137}$ to $Asn_{137}$ to obtain the $Asn_{137}XI$ mutein, 5'-

CTCGCGGCCGCCGTTGGCCACATAGGTC-3';

to convert Trp$_{137}$ to Gln$_{137}$ to obtain the Gln$_{137}$XI mutein, 5'-CTCGCGGCCGCCCTGGGCCACATAGGTC-3';

to convert Trp$_{137}$ to Ser$_{137}$ to obtain the Ser$_{137}$XI mutein, 5'-CTCGCGGCCGCCCGAGGCCACATAGGTC-3';

to convert Trp$_{137}$ to Thr$_{137}$ to obtain the Thr$_{137}$XI mutein, 5'-CTCGCGGCCGCCCGTGGCCACATAGGTC-3';

to convert Trp$_{137}$ to Gly$_{137}$ to obtain the Gly$_{137}$XI mutein, 5'-CTCGCGGCCGCCCCCGGCCACATAGGTC-3';

to convert Trp$_{137}$ to Ala$_{137}$ to obtain the Ala$_{137}$XI mutein, 5'-CTCGCGGCCGCCCGCGGCCACATAGGTC-3';

to convert Trp$_{137}$ to Val$_{137}$ to obtain the Val$_{137}$XI mutein, 5'-CTCGCGGCCGCCCACGGCCACATAGGTC-3';

to convert Trp$_{137}$ to Leu$_{137}$ to obtain the Leu$_{137}$XI mutein, 5'-CTCGCGGCCGCCCAGGGCCACATAGGTC-3';

to convert Trp$_{137}$ to Ile$_{137}$ to obtain the Ile$_{137}$XI mutein, 5'-CTCGCGGCCGCCGATGGCCACATAGGTC-3';

to convert Trp$_{137}$ to Tyr$_{137}$ to obtain the Tyr$_{137}$XI mutein, 5'-CTCGCGGCCGCCGTAGGCCACATAGGTC-3';

to convert Trp$_{137}$ to Phe$_{137}$ to obtain the Phe$_{137}$XI mutein, 5'-CTCGCGGCCGCCGAAGGCCACATAGGTC-3';

to convert Trp$_{137}$ to His$_{137}$ to obtain the His$_{137}$XI mutein, 5'-CTCGCGGCCGCCGTGGGCCACATAGGTC-3';

to convert Phe$_{94}$ to Thr$_{94}$ to obtain the Thr$_{94}$XI mutein, 5'-CACCGGGTGGGTGGTCAGGTTGGTGGTG-3';

to convert Phe$_{94}$ to Ser$_{94}$ to obtain the Ser$_{94}$XI mutein, 5'-CACCGGGTGGGTGGACAGGTTGGTGGTG-3';

to convert Phe$_{94}$ to His$_{94}$ to obtain the His$_{94}$XI mutein, 5'-CACCGGGTGGGTGTGCAGGTTGGTGGTG-3';

to convert Phe$_{94}$ to Val$_{94}$ to obtain the Val$_{94}$XI mutein, 5'-CACCGGGTGGGTGACCAGGTTGGTGGTG-3';

to convert Phe$_{94}$ to Gly$_{94}$ to obtain the Gly$_{94}$XI mutein, 5'-CACCGGGTGGGTGCCAGGTTGGTGGTG-3';

to convert Phe$_{94}$ to Ala$_{94}$ to obtain the Ala$_{94}$XI mutein, 5'-CACCGGGTGGGTGGCCAGGTTGGTGGTG-3';

to convert phe$_{94}$ to Ile$_{94}$ to obtain the Ile$_{94}$XI mutein, 5'-CACCGGGTGGGTGATCAGGTTGGTGGTG-3' to convert Phe$_{94}$ to Leu$_{94}$ to obtain the Leu$_{94}$XI mutein, 5'-CACCGGGTGGGTGAGCAGGTTGGTGGTG-3';

to convert Phe$_{94}$ to Asn$_{94}$ to obtain the Asn$_{94}$XI mutein, 5'-CACCGGGTGGGTGTTCAGGTTGGTGGTG-3'; and/or to convert phe$_{94}$ to Gln$_{94}$ to obtain the Gln$_{94}$XI mutein, 5'-CACCGGGTGGGTCTGCAGGTTGGTGGTG-3'.

EXAMPLE IX

Site-Specific Mutagenesis of the Xylose Isomerase Gene To Produce Muteins Having Increased Stability The procedure of Example VII is followed in substantial detail, except that the mutagenesis primers differ. Second strand synthesis and recovery of the desired XI muteins uses Glycine residues to Alanine residues:

to convert Gly$_{146}$ to Ala$_{146}$ to obtain the Ala$_{146}$XI mutein, 5'-GCACGTCCTTGGCGCCGGCCGACTCGGCACCC-3';

to convert Gly$_{166}$ to Ala$_{166}$ to obtain the Ala$_{166}$XI mutein, 5'-GGTGACGTACTCGGCGACCAGGTCGAAG-3';

to convert Gly$_{197}$ to Ala$_{197}$ to obtain the Ala$_{197}$XI mutein, 5'-CGCCAGGGCGTGGGCGACGGTGGGGAGC-3';

to convert Gly$_{219}$ to Ala$_{219}$ to obtain the Ala$_{219}$XI mutein, 5'-CCATCTGCTCGTGGGCGACCTCGGGGTTC-3';

to convert Gly$_{231}$ to Ala$_{231}$ to obtain the Ala$_{231}$XI mutein, 5'-GCGCCTGCGCGATCGCGTGCGGGAAGTTC-3';

to convert Gly$_{248}$ to Ala$_{248}$ to obtain the Ala$_{248}$XI mutein, 5'-GATGCCGTTCTGGGCGTTGAGGTCG-3';

to convert Gly$_{298}$ to Ala$_{298}$ to obtain the Ala$_{298}$XI mutein, 5'-GAGGCCCACACCGCGTCGAAGTCCTC-3';

to convert Gly$_{305}$ to Ala$_{305}$ to obtain the Ala$_{305}$XI mutein, 5'-GTTGCGCATGCAGGCGGCCGCCGAGG-3'; and/or to convert Gly$_{369}$ to Ala$_{369}$ to obtain the Ala$_{369}$XI mutein, 5'-GCTCGAAGGCCATCGCACGGGCCGCCGCC-3'

The following primers are used to introduce proline residues to produce thermostable xylose isomerase muteins:

to convert Leu$_{15}$ to Pro$_{15}$ to obtain the Pro$_{15}$XI mutein, 5'-CCGACGGTCCACGGTCCGAAGGTG-3';

to convert Asp$_{28}$ to Pro$_{28}$ to obtain the Pro$_{28}$XI mutein, 5'-GCCGCGTGGCGGGACCGAAGGGGTCC-3';

to convert Ala$_{29}$ to Pro$_{29}$ to obtain the Pro$_{29}$XI mutein, 5'-GCGCCGCGTGGGGTCACCGAAGGGG-3';

to convert Arg$_{32}$ to Pro$_{32}$ to obtain the Pro$_{32}$XI mutein, 5'-CCGGGTCGAGGGCCGGCCGCGTGGCGTC-3';

to convert Ala$_{33}$ to Pro$_{33}$ to obtain the Pro$_{33}$XI mutein, 5'-CCGGGTCGAGGGGGCGCCGCGTGG-3';

to convert Ser$_{64}$ to Pro$_{64}$ to obtain the Pro$_{64}$XI mutein, 5'-GCTCGCTGTCGGGGGAGCCGAAGGGG-3';

to convert Asn$_{107}$ to Pro$_{107}$ to obtain the Pro$_{107}$XI mutein, 5'-CGTCGCGGTCGGGGGCGGTGAAGC-3';

to convert Arg$_{109}$ to Pro$_{109}$ to obtain the Pro$_{109}$XI mutein, 5'-GTAGCGGCGCACGTCGGGGTCGTTGGCGGTG-3';

to convert Gly$_{146}$ to Pro$_{146}$ to obtain the Pro$_{146}$XI mutein, 5'-GCACGTCCTTGGCGCCGGGCGACTCGGCACCC-3';

to convert Val₁₅₁ to Pro₁₅₁ to obtain the Pro₁₅₁XI mutein, 5'-GAGGGCGTCCCGCGGGTCCTTGGCGCC-3';

to convert Gly₁₈₉ to Pro₁₈₉ to obtain the Pro₁₈₉XI mutein, 5'-GAGCAGGATGTCGGGGCGCGGCTCGTTC-3';

to convert Leu₁₉₂ to Pro₁₉₂ to obtain the Pro₁₉₂XI mutein, 5'-CGGTGGGGAGCGGGATGTCGCCGCG-3';

to convert Glu₂₀₇ to Pro₂₀₇ to obtain the Pro₂₀₇XI mutein, 5'-CAGCTCCGGTCGCGGCAGGCGCTCGATG-3';

to convert Val₂₁₈ to Pro₂₁₈ to obtain the Pro₂₁₈XI mutein, 5'-GCTCGTGGCCGGGCTCGGGGTTCACGC-3';

to convert Ile₂₅₂ to Pro₂₅₂ to obtain the Pro₂₅₂XI mutein, 5'-GGTCGTACTTGGGGCCGTTCTGGCCG-3';

to convert Arg₂₅₉ to Pro₂₅₉ to obtain the Pro₂₅₉XI mutein, 5'-CCCGCGCCGAAGGGGAGGTCCTGGTC-3';

to convert Arg₂₉₂ to Pro₂₉₂ to obtain the Pro₂₉₂XI mutein, 5'-GAAGTCCTCGGTCGGCGGCGGCTTGAAG-3';

to convert Thr₃₄₂ to Pro₃₄₂ to obtain the Pro₃₄₂XI mutein, 5'-CGTAGGCCGCCGGGGGCCGGGCCAG-3';

to convert Arg₃₅₄ to Pro₃₅₄ to obtain the Pro₃₅₄XI mutein, 5'-CGAAGGCGGACGGGTCGTCGAGCAGG-3'; and/or to convert Gly₃₆₉ to Pro₃₆₉ to obtain the Pro₃₆₉XI mutein, 5'-GCTCGAAGGCCATGGGACGGGCCGCCGCC-3'.

The following primers are used to introduce aromatic amino acid residues to produce thermostable xylose isomerase muteins:

to convert Asp9 to Tyr9 to obtain the Tyr₉XI mutein, 5'-GGTGAACCTGTACTCGGGGGTGGGC-3';

to convert Gln2l to Tyr₂l to obtain the Tyr₂XI mutein, 5'-GGGGTCCCGTCCGTACCAGCCGACGGTCC-3';

to convert Ala₂₉ to Tyr₂₉ to obtain the Tyr₂₉XI mutein, 5'-GGCGCGCCGCGTGTAGTCACCGAAGGGG-3';

to convert Arg₃₂ to Tyr₃₂ to obtain the Tyr₃₂XI mutein, 5'-GGGTCGAGGGCGTACCGCGTGGCGTCAC-3';

to convert Glu₃₈ to Tyr₃₈ to obtain the Tyr₃₈XI mutein, 5'-CCGCCGCACCGAGTAGACCGGGTCGAGGG-3'; 'to convert Leu₄₆ to Phe₄₆ to obtain the Phe₄₆XI mutein, 5'-GCCGTGGGCGCCGAACTCGGCCAGCCGCC-3';

to convert Leu₄₆ to Tyr₄₆ to obtain the Tyr₄₆XI mutein, 5'-GCCGTGGGCGCCGTACTCGGCCAGCCGCC-3';

to convert Asp₅₆ to Phe₅₆ to obtain the Phe₅₆XI mutein, 5'-GGGGATGAGGTCGAAGTCGTGGAACGTG-3';

to convert Asp₅₆ to Tyr₅₆ to obtain the Tyr₅₆XI mutein, 5'-GGGGATGAGGTCGTAGTCGTGGAACGTG-3';

to convert Leu₅₈ to Phe₅₈ to obtain the Phe₅₈XI mutein, 5'-GCCGAAGGGGATGAAGTCGTCGTCGTGG-3';

to convert Leu₅₈ to Tyr₅₈ to obtain the Tyr₅₈XI mutein, 5'-GCCGAAGGGGATGTAGTCGTCGTCGTGG-3';

to convert Val₁₂₇ to Tyr₁₂₇ to obtain the Tyr₁₂₇XI mutein, 5'-GGCGCCGAGCTCGTACGCGAGGTCGATG-3';

to convert Thr₁₃₃ to Phe₁₃₃ to obtain the Phe₁₃₃XI mutein, 5'-CCAGGCCACATAGAACTCGGCGCCGAGCTC-3';

to convert Thr₁₃₃ to Tyr₁₃₃ to obtain the Tyr₁₃₃XI mutein, 5'-CCAGGCCACATAGTACTCGGCGCCGAGCTC-3' to convert Ala₁₃₆ to Phe₁₃₆ to obtain the Phe₁₃₆XI mutein, 5'-GGCCGCCCCAGAACACATAGGTCTCGG-3' to convert Ala₁₃₆ to Tyr₁₃₆ to obtain the Tyr₁₃₆XI mutein, 5'-GGCCGCCCCAGTACACATAGGTCTCGG-3' to convert Arg₁₇₇ to Tyr₁₇₇ to obtain the Tyr₁₇₇XI mutein, 5'-GCTCGATGGCGAAGTAGATGTCGTAGCCC-3';

to convert Ile₁₈₀ to Phe₁₈₀ to obtain the Phe₁₈₀XI mutein, 5'-CGGCTTGGGCTCGAAGGCGAAGCGGATG-3';

to convert Ile₁₈₀ to Tyr₁₈₀ to obtain the Tyr₁₈₀XI mutein, 5'-CGGCTTGGGCTCGTAGGCGAAGCGGATG-3';

to convert Leu₁₉₃ to Phe₁₉₃ to obtain the Phe₁₉₃XI mutein, 5'-CCGACGGTGGGGAACAGGATGTCGCC-3';

to convert Leu₁₉₃ to Tyr₁₉₃ to obtain the Tyr₁₉₃XI mutein, 5'-CCGACGGTGGGGTACAGGATGTCGCC-3';

to convert Leu₂₁₁ to Phe₂₁₁ to obtain the Phe₂₁₁XI mutein, 5'-GGTTCACGCCGTAGAACTCCGGTCGCTCC-3';

to convert Leu₂₁₁ to Tyr₂₁₁ to obtain the Tyr₂₁₁XI mutein, 5'-GGTTCACGCCGTAGTACTCCGGTCGCTCC-3';

to convert Asn227 to Phe₂₂₇ to obtain the Phe₂₂₇XI mutein, 5'-GCCGTGCGGGAAGAACAGCCCGGCCATC-3';

to convert Asn227 to Tyr₂₂₇ to obtain the Tyr₂₂₇XI mutein, 5'-GCCGTGCGGGAAGTACAGCCCGGCCATC-3';

to convert Asn227 to Trp₂₂₇ to obtain the Trp₂₂₇XI mutein, 5'-GCCGTGCGGGAACCACAGCCCGGCCATC-3';

to convert Gln₂₃₄ to Phe₂₃₄ to obtain the Phe₂₃₄XI mutein, 5'-CCGCCCACAGCGCGAACGCGATGCCGTG-3';

to convert Gln₂₃₄ to Tyr₂₃₄ to obtain the Tyr₂₃₄XI mutein, 5'-CCGCCCACAGCGCGTACGCGATGCCGTG-3';

to convert Ala₂₃₈ to Phe₂₃₈ to obtain the Phe₂₃₈XI mutein, 5'-GGAACAGCTTGCCGAACCACAGCGCCTGC-3';

to convert Ala₂₃₈ to Tyr₂₃₈ to obtain the Tyr₂₃₈XI mutein, 5'-GGAACAGCTTGCCGTACCACAGCGCCTGC-3';

to convert Leu₂₄₆ to Phe₂₄₆ to obtain the Phe₂₄₆XI mutein, 5'-GTTCTGGCCGTTGAAGTCGATGTGGAAC-3';

to convert Leu₂₄₆ to Tyr₂₄₆ to obtain the Tyr₂₄₆XI mutein, 5'-GTTCTGGCCGTTGTAGTCGATGTGGAAC-3';

to convert Arg₂₈₄ to Phe₂₈₄ to obtain the Phe₂₈₄XI mutein, 5'-GAAGTCGAAGTGGTACGGGCCGCTGTAGC-3';

to convert Arg$_{308}$ to Tyr$_{308}$ to obtain the Tyr$_{308}$XI mutein, 5'-GGATCAGGTAGTTGTACATG-CAGCCGG3;

to convert Leu$_{311}$ to Phe$_{311}$ to obtain the Phe$_{311}$XI mutein, 5'-CGCTCCTTGAGGATGAAG-TAGTTGCGCATGC-3';

to convert Leu$_{311}$ to Tyr$_{311}$ to obtain the Tyr$_{311}$XI mutein, 5'-CGCTCCTTGAGGATGTAG-TAGTTGCGCATGC-3';

to convert Arg$_{316}$ to Tyr$_{316}$ to obtain the Tyr$_{316}$XI mutein, 5'-GAAGGCCGCCGCGTACTCCTT-GAGGATC-3';

to convert Leu$_{335}$ to Phe$_{335}$ to obtain the Phe$_{335}$XI mutein, 5'-GCCAGCTCGTCGAAACG-GGACGCGC-3';

to convert Leu$_{335}$ to Tyr$_{335}$ to obtain the Tyr$_{335}$XI mutein, 5'-GCCAGCTCGTCGTAACG-GGACGCGC-3';

to convert Val$_{362}$ to Phe$_{362}$ to obtain the Phe$_{362}$XI mutein, 5'-GCCGCCGCGTCGAAGT-CGAACTCCTCG-3';

to convert Val$_{362}$ to Tyr$_{362}$ to obtain the Tyr$_{362}$XI mutein, 5'-GCCGCCGCGTCGTAGT-CGAACTCCTCG-3';

to convert Met$_{370}$ to Phe$_{370}$ to obtain the Phe$_{370}$XI muetin, 5'-CGCTCGAAGGCGAACCCACGGGCCG-3';

to convert Met$_{370}$ to Tyr$_{370}$ to obtain the Tyr$_{370}$XI mutein, 5'-CGCTCGAAGGCGTACC-CACGGGCCG-3';

to convert Leu$_{375}$ to Phe$_{375}$ to obtain the Phe$_{375}$XI mutein, 5'-CGCCAGCTGGTCGAAGCGCT-CGAAGGC-3';

to convert Leu$_{375}$ to Tyr$_{375}$ to obtain the Tyr$_{375}$XI mutein, 5'-CGCCAGCTGGTCGTAGCGCT-CGAAGGC-3';

to convert Leu$_{383}$ to Phe$_{383}$ to obtain the Phe$_{383}$XI mutein, 5'-CGGGCGCCCAGGAAGTGGT-CCATCGC-3'; and/or to convert Leu$_{383}$ to Tyr$_{383}$ to obtain the Tyr$_{383}$XI mutein, 5'-CGGGCGCCCAGGTAGTGGT-CCATCGC-3'.

The following primers are used to substitute amino acid residues for residues that are located near the interface of subunits of the xylose isomerase protein that may undergo deamidation, to produce xylose isomerase muteins more stable toward irreversible thermal inactivation:

to convert Gln$_{21}$ to Ala$_{21}$ to obtain the Ala$_{21}$XI mutein, 5'-GGGGTCCCGTCCGGCCCAGC-CGACGGTCC-3';

to convert Gln$_{21}$ to Val$_{121}$ to obtain the Val$_{21}$XI mutein, 5'-GGGGTCCCGTCCGACCCAGC-CGACGGTCC-3';

to convert Gln$_{21}$ to Leu$_{21}$ to obtain the Leu$_{21}$XI mutein, 5'-GGGGTCCCGTCCGAGCCAGC-CGACGGTCC-3';

to convert Gln$_{21}$ to Ile$_{21}$ to obtain the Ile$_{21}$ mutein, 5'-GGGGTCCCGTCCGATCCAGC-CGACGGTCC 3';

to convert Gln$_{21}$ to Ser$_{21}$ to obtain the Ser$_{21}$ mutein, 5'-GGGGTCCCGTCCGCTCCAGC-CGACGGTCC-3';

to convert Gln$_{21}$ to Thr$_{21}$ to obtain the Thr$_{21}$ mutein, 5'-GGGGTCCCGTCCGGTCCAGC-CGACGGTCC-3';

to convert Gln$_{21}$ to His$_{21}$ to obtain the His$_{21}$ mutein, 5'-GGGGTCCCGTCCGTGCCAGC-CGACGGTCC-3';

to convert Gln$_{21}$ to Tyr$_{21}$ to obtain the Tyr$_{21}$ mutein, 5'-GGGGTCCCGTCCGTACCAGC-CGACGGTCC-3';

to convert Gln$_{21}$ to Lys$_{21}$ to obtain the Lys$_{21}$ mutein, 5'-GGGGTCCCGTCCCTTCCAGC-CGACGGTCC-3';

to convert Gln$_{21}$ to Arg$_{21}$ to obtain the Arg$_{21}$ mutein, 5'-GGGGTCCCGTCCGCGCCAGC-CGACGGTCC-3';

to convert Gln$_{21}$ to Met$_{21}$ to obtain the Met$_{21}$ mutein, 5'-GGGGTCCCGTCCCATCCAGC-CGACGGTCC-3';

to convert Gln$_{21}$ to Pro$_{21}$ to obtain the Pro$_{21}$ mutein, 5'-GGGGTCCCGTCCGGGCCAGC-CGACGGTCC-3';

to convert Asn$_{92}$ to Ala$_{92}$ to obtain the Ala$_{92}$ mutein, 5'-GGTGGGTGAACAGGGCGGTGGTGG-CCATCG-3' to convert Asn$_{92}$ to Val$_{192}$ to obtain the Val$_{92}$ mutein, 5'-GGTGGGTGAACAGGACGGTGGTGG-CCATCG-3';

to convert Asn$_{92}$ to Leu$_{92}$ to obtain the Leu$_{92}$ mutein, 5'-GGTGGGTGAACAGGAGGGTGGTGG-CCATCG-3';

to convert Asn$_{92}$ to Ile$_{92}$ to obtain the Ile$_{92}$ mutein, 5'-GGTGGGTGAACAGGATGGTGGTGG-CCATCG-3';

to convert Asn$_{92}$ to Ser$_{92}$ to obtain the Ser$_{92}$XI mutein, 5'-GGTGGGTGAACAGGCTGGTGGTGG-CCATCG-3';

to convert Asn$_{92}$ to Thr$_{92}$ to obtain the Thr$_{92}$XI mutein, 5'-GGTGGGTGAACAGGGTGGTGGTGG-CCATCG-3';

to convert Asn$_{92}$ to His$_{92}$ to obtain the His$_{92}$XI mutein, 5'-GGTGGGTGAACAGGTGGGTGGTGG-CCATCG-3';

to convert Asn$_{92}$ to Tyr$_{92}$ to obtain the Tyr$_{92}$XI mutein, 5'-GGTGGGTGAACAGGTAGGTGGTGG-CCATCG-3';

to convert Asn$_{92}$ to Lys$_{92}$ to obtain the Lys$_{92}$XI mutein, 5'-GGTGGGTGAACAGCTTGGTGGTGG-CCATCG-3';

to convert Asn$_{92}$ to Arg$_{92}$ to obtain the Arg$_{92}$XI mutein, 5'-GGTGGGTGAACAGGCGGGTGGTGG-CCATCG-3';

to convert Asn$_{92}$ to Met$_{92}$ to obtain the Met$_{92}$XI mutein, 5'-GGTGGGTGAACAGCATGGTGGTGG-CCATCG-3';

to convert Asn$_{92}$ to Pro$_{92}$ to obtain the Pro$_{92}$XI mutein, 5'-GGTGGGTGAACAGGGGGGTGGTGG-CCATCG-3';

to convert Asn$_{107}$ to Ala$_{107}$ to obtain the Ala$_{107}$XI mutein, 5'-GCACGTCGCGGTCGGCGGCGGT-GAAGCCG-3';

to convert Asn$_{107}$ to Val$_{107}$ to obtain the Val$_{107}$XI mutein, 5'-GCACGTCGCGGTCGACGGCGGT-GAAGCCG-3';

to convert Asn$_{107}$ to Leu$_{107}$ to obtain the Leu$_{107}$XI mutein, 5'-GCACGTCGCGGTCGAGGGCGGT-GAAGCCG-3';

to convert Asn$_{107}$ to Ile$_{107}$ to obtain the Ile$_{107}$XI mutein, 5'-GCACGTCGCGGTCGATGGCGGT-GAAGCCG-3';

to convert $Asn_{107}$ to $Ser_{107}$ to obtain the $Ser_{107}$XI mutein, 5'-GCACGTCGCGGTCGCTGGCGGT-GAAGCCG-3';

to convert $Asn_{107}$ to $Thr_{107}$ to obtain the $Thr_{107}$XI mutein, 5'-GCACGTCGCGGTCGGTGGCGGT-GAAGCCG-3';

to convert $Asn_{107}$ to $His_{107}$ to obtain the $His_{107}$XI mutein, 5'-GCACGTCGCGGTCGTGGGCGGT-GAAGCCG-3';

to convert $Asn_{107}$ to $Tyr_{107}$ to obtain the $Tyr_{107}$XI mutein, 5'-GCACGTCGCGGTCGTAGGCGGT-GAAGCCG-3';

to convert $Asn_{107}$ to $Lys_{107}$ to obtain the $Lys_{107}$XI mutein, 5'-GCACGTCGCGGTCCTTGGCGGT-GAAGCCG-3' to convert $Asn_{107}$ to $Arg_{107}$ to obtain the $Arg_{107}$XI mutein, 5'-GCACGTCGCGGTCGCGGGCGGT-GAAGCCG-3';

to convert $Asn_{107}$ to $Met_{107}$ to obtain the $Met_{107}$XI mutein, 5'-GCACGTCGCGGTCCATGGCGGT-GAAGCCG-3';

to convert $Asn_{107}$ to $Pro_{107}$ to obtain the $Pro_{107}$XI mutein, 5'-GCACGTCGCGGTCGGGGGCGGT-GAAGCCG-3';

to convert $Asn_{185}$ to $Ala_{185}$ to obtain the $Ala_{185}$XI mutein, 5'-CGCCGCGCGGCTCGGCCGGCTTGGGCTC-G-3';

to convert $Asn_{185}$ to $Val_{1185}$ to obtain the $Val_{1185}$XI mutein, 5'-CGCCGCGCGGCTCGACCGGCTTGGGCTC-G-3' to convert $Asn_{185}$ to $Leu_{185}$ to obtain the $Leu_{185}$XI mutein, 5'-CGCCGCGCGGCTCGAGCGGCTTGGGCTC-G-3';

to convert $Asn_{185}$ to $Ile_{185}$ to obtain the $Ile_{185}$XI mutein, 5'-CGCCGCGCGGCTCGATCGGCTTGGGCTC-G-3' to convert $Asn_{185}$ to $Ser_{185}$ to obtain the $Ser_{185}$XI mutein, 5'-CGCCGCGCGGCTCGCTCGGCTTGGGCTCG-3';

to convert $Asn_{185}$ to $Thr_{185}$ to obtain the $Thr_{185}$XI mutein, 5'-CGCCGCGCGGCTCGGTCGGCTTGGGCTC-G-3';

to convert $Asn_{185}$ to $His_{185}$ to obtain the $His_{185}$XI mutein, 5'-CGCCGCGCGGCTCGTGCGGCTTGGGCTC-G-3';

to convert $Asn_{185}$ to $Tyr_{185}$ to obtain the $Tyr_{185}$XI mutein, 5'-CGCCGCGCGGCTCGTACGGCTTGGGCTC-G3;

to convert $Asn_{185}$ to $Lys_{185}$ to obtain the $Lys_{185}$XI mutein, T'CGCCGCGCGGCTCCTTCGGCTTGGGCTC-G-3';

to convert $Asn_{185}$ to $Arg_{185}$ to obtain the $Arg_{185}$XI mutein, 5'-CGCCGCGCGGCTCGCGCGGCTTGGGCTC-G-3';

to convert $Asn_{185}$ to $Met_{185}$ to obtain the $Met_{185}$XI mutein, 5'-CGCCGCGCGGCTCCATCGGCTTGGGCTCG-3';

to convert $Asn_{185}$ to $Pro_{185}$ to obtain the $Pro_{185}$XI mutein, 5'-CGCCGCGCGGCTCGGGCGGCTTGGGCTC-G-3';

to convert $Asn_{227}$ to $Ala_{227}$ to obtain the $Ala_{227}$XI mutein, 5'-GCCGTGCGGGAAGGCCAGCCCGG-CCATC-3';

to convert $Asn_{227}$ to $Val_{1227}$ to obtain the $Val_{1227}$XI mutein, 5'-GCCGTGCGGGAAGAC-CAGCCCGGCCATC-3';

to convert $Asn_{227}$ to $Leu_{227}$ to obtain the $Leu_{227}$XI mutein, 5'-GCCGTGCGGGAAGAG-CAGCCCGGCCATC-3';

to convert $Asn_{227}$ to $Ile_{227}$ to obtain the $Ile_{227}$XI mutein, 5'-GCCGTGCGGGAAGATCAGCCCGG-CCATC3 to convert $Asn_{227}$ to $Ser_{227}$ to obtain the $Ser_{227}$XI mutein, 5'-GCCGTGCGGGAAGCTCAGCCCGG-CCATC-3';

to convert $Asn_{227}$ to $Thr_{227}$ to obtain the $Thr_{227}$XI mutein, 5'-GCCGTGCGGGAAGGTCAGCCCGG-CCATC-3';

to convert $Asn_{227}$ to $His_{227}$ to obtain the $His_{227}$XI mutein, 5'-GCCGTGCGGGAAGTGCAGCCCGG-CCATC-3';

to convert $Asn_{227}$ to $Tyr_{227}$ to obtain the $Tyr_{227}$XI mutein, 5'-GCCGTGCGGGAAGTACAGCCCGG-CCATC-3';

to convert $Asn_{227}$ to $Lys_{227}$ to obtain the $Lys_{227}$XI mutein, 5'-GCCGTGCGGGAACTTCAGCCCGG-CCATC-3';

to convert $Asn_{227}$ to $Arg_{227}$ to obtain the $Arg_{227}$XI mutein, 5'-GCCGTGCGGGAAGC-GCAGCCCGGCCATC-3';

to convert $Asn_{227}$ to $Met_{227}$ to obtain the $Met_{227}$XI mutein, 5'-GCCGTGCGGGAACAT-CAGCCCGGCCATC-3';

to convert $Asn_{227}$ to $Pro_{227}$ to obtain the $Pro_{227}$XI mutein, 5'-GCCGTGCGGGAAGGGCAGCCCGG-CCATC-3';

to convert $Gln_{234}$ to $Ala_{234}$ to obtain the $Ala_{234}$XI mutein, 5'-CGCCCACAGCGCGGCCG-CGATGCCGTGCG-3';

to convert $Gln_{234}$ to $Val_{1234}$ to obtain the $Val_{1234}$XI mutein, 5'-CGCCCACAGCGCGACCG-CGATGCCGTGCG-3';

to convert $Gln_{234}$ to $Leu_{234}$ to obtain the $Leu_{234}$XI mutein, 5'-CGCCCACAGCGCGAGCG-CGATGCCGTGCG-3';

to convert $Gln_{234}$ to $Ile_{234}$ to obtain the $Ile_{234}$XI mutein, 5'-CGCCCACAGCGCGATCG-CGATGCCGTGCG-3';

to convert $Gln_{234}$ to $Ser_{234}$ to obtain the $Ser_{234}$XI mutein, 5'-CGCCCACAGCGCGCTCG-CGATGCCGTGCG-3';

to convert $Gln_{234}$ to $Thr_{234}$ to obtain the $Thr_{234}$XI mutein, 5'-CGCCCACAGCGCGGTCG-CGATGCCGTGCG-3';

to convert $Gln_{234}$ to $His_{234}$ to obtain the $His_{234}$XI mutein, 5'-CGCCCACAGCGCGTGCG-CGATGCCGTGCG-3';

to convert $Gln_{234}$ to $Tyr_{234}$ to obtain the $Tyr_{234}$XI mutein, 5'-CGCCCACAGCGCGTACG-CGATGCCGTGCG-3';

to convert $Gln_{234}$ to $Lys_{234}$ to obtain the $Lys_{234}$XI mutein, 5'-CGCCCACAGCGCCTTCG-CGATGCCGTGCG-3';

to convert Gln$_{234}$ to Arg$_{234}$ to obtain the Arg$_{234}$XI mutein, 5'-CGCCCACAGCGCGCGCGATGCCGTGCG-3' to convert Gln$_{234}$ to Met$_{234}$ to obtain the Met$_{234}$XI mutein, 5'-CGCCCACAGCGCCATCGCGATGCCGTGCG-3';

to convert Gln$_{234}$ to Pro$_{234}$ to obtain the Pro$_{234}$XI mutein, 5'-CGCCCACAGCGCGGGCGCGATGCCGTGCG-3';

Gln$_{256}$ to Ala$_{256}$ to obtain the Ala$_{256}$XI mutein, 5,-CGAAGCGGAGGTCGGCGTCGTACTTGATGC-3';

to convert Gln$_{256}$ to Val$_{1256}$ to obtain the Val$_{1256}$XI mutein, 5'-CGAAGCGGAGGTCGACGTCGTACTTGATGC-3';

to convert Gln$_{256}$ to Leu$_{256}$ to obtain the Leu$_{256}$XI mutein, 5'-CGAAGCGGAGGTCGAGGTCGTACTTGATGC-3';

to convert Gln$_{256}$ to Ile$_{256}$ to obtain the Ile$_{256}$XI mutein, 5'-CGAAGCGGAGGTCGATGTCGTACTTGATGC-3';

to convert Gln$_{256}$ to Ser$_{256}$ to obtain the Ser$_{256}$XI mutein, 5'-CGAAGCGGAGGTCGCTGTCGTACTTGATGC-3';

to convert Gln$_{256}$ to Thr$_{256}$ to obtain the Thr$_{256}$XI mutein, 5'-CGAAGCGGAGGTCGGTGTCGTACTTGATGC-3';

to convert Gln$_{256}$ to His$_{256}$ to obtain the His$_{256}$XI mutein, 5'-CGAAGCGGAGGTCGTGGTCGTACTTGATGC-3';

to convert Gln$_{256}$ to Tyr$_{256}$ to obtain the Tyr$_{256}$XI mutein, 5'-CGAAGCGGAGGTCGTAGTCGTACTTGATGC-3';

to convert Gln$_{256}$ to Lys$_{256}$ to obtain the Lys$_{256}$XI mutein, 5'-CGAAGCGGAGGTCCTTGTCGTACTTGATGC-3';

to convert Gln$_{256}$ to Arg$_{256}$ to obtain the Arg$_{256}$XI mutein, 5'-CGAAGCGGAGGTCGCGGTCGTACTTGATGC-3';

to convert Gln$_{256}$ to Met$_{256}$ to obtain the Met$_{256}$XI mutein, 5'-CGAAGCGGAGGTCCATGTCGTACTTGATGC-3';

to convert Gln$_{256}$ to Pro$_{256}$ to obtain the Pro$_{256}$XI mutein, 5'-CGAAGCGGAGGTCGGGGTCGTACTTGATGC-3';

to convert Asn$_{309}$ to Ala$_{309}$ to obtain the Ala$_{309}$XI mutein, 5'-GAGGATCAGGTAGGCGCGCATGCAGCCGGC-3';

to convert Asn$_{309}$ to Val$_{309}$ to obtain the Val$_{309}$XI mutein, 5,-GAGGATCAGGTAGACGCGCATGCAGCCGGC-3';

to convert Asn$_{309}$ to Leu$_{309}$ to obtain the Leu$_{309}$XI mutein, 5'-GAGGATCAGGTAGAGGCGCATGCAGCCGGC-3';

to convert Asn$_{309}$ to Ile$_{309}$ to obtain the Ile$_{309}$XI mutein, 5'-GAGGATCAGGTAGATGCGCATGCAGCCGGC-3';

to convert Asn$_{309}$ to Ser$_{309}$ to obtain the Ser$_{309}$XI mutein, 5'-GAGGATCAGGTAGCTGCGCATGCAGCCGGC-3';

to convert Asn$_{309}$ to Thr$_{309}$ to obtain the Thr$_{309}$XI mutein, 5'-GAGGATCAGGTAGGTGCGCATGCAGCCGGC-3';

to convert Asn$_{309}$ to His$_{309}$ to obtain the His$_{309}$XI mutein, 5'-GAGGATCAGGTAGTGGCGCATGCAGCCGGC-3';

to convert Asn$_{309}$ to Tyr$_{309}$ to obtain the Tyr$_{309}$XI mutein, 5'-GAGGATCAGGTAGTAGCGCATGCAGCCGGC-3';

to convert Asn$_{309}$ to Lys$_{309}$ to obtain the Lys$_{309}$XI mutein, 5'-GAGGATCAGGTACTTGCGCATGCAGCCGGC-3';

to convert Asn$_{309}$ to Arg$_{309}$ to obtain the Arg$_{309}$XI muetin, 5'-GAGGATCAGGTAGCGGCGCATGCAGCCGGC-3';

to convert Asn$_{309}$ to Met$_{309}$ to obtain the Met$_{309}$XI mutein, 5'-GAGGATCAGGTACATGCGCATGCAGCCGGC-3';

to convert Asn$_{309}$ to Pro$_{309}$ to obtain the Pro$_{309}$XI mutein, 5'-GAGGATCAGGTAGGGGCGCATGCAGCCGGC-3';

to convert Asn$_{377}$ to Ala$_{377}$ to obtain the Ala$_{377}$XI mutein, 5'-GGTCCATCGCCAGGGCGTCCAGGCGCTCG-3';

to convert Asn$_{377}$ to Val$_{377}$ to obtain the Val$_{377}$XI mutein, 5'-GGTCCATCGCCAGGACGTCCAGGCGCTCG-3';

to convert Asn$_{377}$ to Leu$_{377}$ to obtain the Leu$_{377}$XI mutein, 5'-GGTCCATCGCCAGGAGGTCCAGGCGCTCG-3';

to convert Asn$_{377}$ to Ile$_{377}$ to obtain the Ile$_{377}$XI mutein, 5'-GGTCCATCGCCAGGATGTCCAGGCGCTCG-3';

to convert Asn$_{377}$ to Ser$_{377}$ to obtain the Ser$_{377}$XI mutein, 5'-GGTCCATCGCCAGGCTGTCCAGGCGCTCG-3';

to convert Asn$_{377}$ to Thr$_{377}$ to obtain the Thr$_{377}$XI mutein, 5'-GGTCCATCGCCAGGGTGTCCAGGCGCTCG-3';

to convert Asn$_{377}$ to His$_{377}$ to obtain the His$_{377}$XI mutein, 5'-GGTCCATCGCCAGGTGGTCCAGGCGCTCG-3';

to convert Asn$_{377}$ to Tyr$_{377}$ to obtain the Tyr$_{377}$XI mutein, 5'-GGTCCATCGCCAGGTAGTCCAGGCGCTCG-3';

to convert Asn$_{377}$ to Lys$_{377}$ to obtain the Lys$_{377}$XI mutein, 5'-GGTCCATCGCCAGCTTGTCCAGGCGCTCG-3';

to convert Asn$_{377}$ to Arg$_{377}$ to obtain the Arg$_{377}$XI mutein, 5'-GGTCCATCGCCAGGCGGTCCAGGCGCTCG-3';

to convert Asn$_{377}$ to Met$_{377}$ to obtain the Met$_{377}$XI mutein, 5'-GGTCCATCGCCAGCATGTCCAGGCGCTCG-3'; and/or to convert Asn$_{377}$ to Pro$_{377}$ to obtain the Pro$_{377}$XI mutein, 5'-GGTCCATCGCCAGGGGGTCCAGGCGCTCG-3'.

The following primers are used to introduce two cysteine residues to produce disulfide bridges in the xylose isomerase protein to create thermostable xylose isomerase muteins:

to convert Trp$_{270}$ to Cys$_{270}$, and Gly$_{146}$ to Cys$_{146}$, 5'-CAGGTCCACCAGGCAGAACGCGGCCCGC-3', and 5'-GTCCTTGGCGCCGCACGACTCGGCACCC-3', to obtain the Cys$_{270}$Cys$_{146}$XI mutein;

to convert Phe$_{320}$ to Cys$_{320}$, and His$_{382}$ to Cys$_{382}$, 5'-GGTCGGCGCGGCAGGCCGCCGCACGC-3', and 5'-CGCCCAGCAGGCAGTCCATCGCCAGC-3', to obtain the Cys$_{320}$Cys$_{382}$XI mutein;

to convert Glu$_{337}$ to Cys$_{337}$, and Arg$_{109}$ to Cys$_{109}$, 5'-GGGCCGGGCCAGGCAGTCCAGACGGGAC-3', and 5'-CGGCGCACGTCGCAGTCGTTGGCGGTG-3', to obtain the Cys$_{337}$Cys$_{109}$XI mutein;

to convert Gly$_{189}$ to Cys$_{189}$, and Glu$_{144}$ to Cys$_{144}$, 5'-GCAGGATGTCGCAGCGCGGCTCGTTC-3', and 5'-GGCGCCACCCGAGCAGG-CACCCTCGCGG-3', to obtain the Cys$_{189}$Cys$_{144}$XI mutein;

to convert Gly$_{251}$ to Cys$_{251}$, and Gly$_{225}$ to Cys$_{225}$, 5'-TCGTACTTGATGCAGTTCTGGCCGTTG-3', and 5'-GCGGGAAGTTCAGGCAGG-CCATCTGCTCG-3', to obtain the Cys$_{251}$Cys$_{225}$XI mutein;

to convert Ala$_{366}$ to Cys$_{366}$, and Val$_{98}$ to Cys$_{98}$, 5'-CCATCCCACGGGCGCACGCCGCGT-CGACG-3', and 5'-CGCCGTCCTTGAAG-CACGGGTGGGTGAAC-3', to obtain the Cys$_{366}$Cys$_{98}$XI mutein;

to convert Gln$_{249}$ to Cys$_{249}$, and Gly$_{219}$ to Cys$_{219}$, 5'-GTACTTGATGCCGTTGCAGCCGTT-GAGGTCG-3'; and 5'-CATCTGCTCGTG-GCAGACCTCGGGGTTC-3', to obtain the Cys$_{249}$Cys$_{219}$XI mutein; and/or to convert Glu$_{207}$ to Cys$_{207}$, and Asp$_{163}$ to Cys$_{163}$, 5'-CAGCTCCGGTCGGCACAGGCGCTCGATG-3', and 5'-CTCGCCGAGCAGG-CAGAAGGCCTCCTTC-3', to obtain the Cys$_{207}$Cys$_{163}$XI mutein.

EXAMPLE IX

Xylose-Isomerase Muteins Exhibiting

Modified Kinetics

The isomerase activity of the reference and xylose isomerase muteins obtained as described above, is assayed using the substrates glucose, fructose, xylose and xylulose. Kinetic measurements are taken of the K$_P$, K$_S$, k$_{catf}$ and k$_{catr}$ for both equilibrium reactions using the HPLC assay previously described. Kinetic parameters are obtained by analysis of the progress curves of the reactions, using a program that carries out a weighted linear or nonlinear least-squares regression analysis of data by using the Lineweaver-Burk or Michaelis-Menten equations, respectively, such as that described by Roberts, in *Enzyme Kinetics*, Cambridge Univ. Press, Cambridge p. 299-306 (1977), incorporated by reference herein. Data is examined for modified enzymes showing a changed specificity, relative to the reference enzyme, toward either glucose or xylose substrate.

EXAMPLE X

Determination of Thermostability of Xylose Isomerase Muteins

Reference XI or XI mutein is produced and purified as described in Example I. The purified protein is adjusted to an average activity of 1.8-2.0 U/ml as determined by HPLC assay, and after precooling in a salt and ice bath, is mixed with glucose solution also precooled (400 g/l glucose, 25 mM maleic acid, 10 mM MgSO$_4$—H$_2$O, 1 mM Fe$^{++}$ (FeSO$_4$.7H$_2$O, pH 6.5) in a 1:1 ratio at 1° C. and distributed into 100 μl thin-walled glass micropipettes (Fisher Scientific, Pittsburgh, Pa.) which are flamed sealed and incubated in heating baths at different isomerization temperatures for 40 minutes. Temperatures of the heating baths are set at 1° C. intervals over the range at which the enzyme shows the full range of inactivation (85° C. to 100° C. for the reference XI). One bath is set at the reference temperature approximately 10° C. below the temperature of half maximum enzyme activity. For the blank samples, the buffer solution is mixed with the glucose substrate in a 1:1 ratio and distributed into 100 μl thin-walled glass micropipettes which are sealed and incubated in water baths at the same temperatures and incubation time as used for the enzyme test samples. The reaction is terminated by immersing the micropipettes in a salt-ice bath, and 65 μl of isomerase is removed from each micropipette. 2 μl of 1N HCl is added to stop the isomerase reaction. The isomerase is assayed for fructose and glucose by HPLC using a Beckman Liquid Chromatograph as described in Example I.

The HPLC results are calculated as the degree of isomerization ($I_T$) at each temperature as follows:

$$I_T = \frac{F}{F + G}$$

F = (% fructose in sample − % fructose in blank)
G = (% glucose in sample)

The percent dry basis fructose data is used to calculate the temperature at which the half-life is 20 minutes [T$_{20}$] as a measure of thermostability, as follows.

Figure 4:
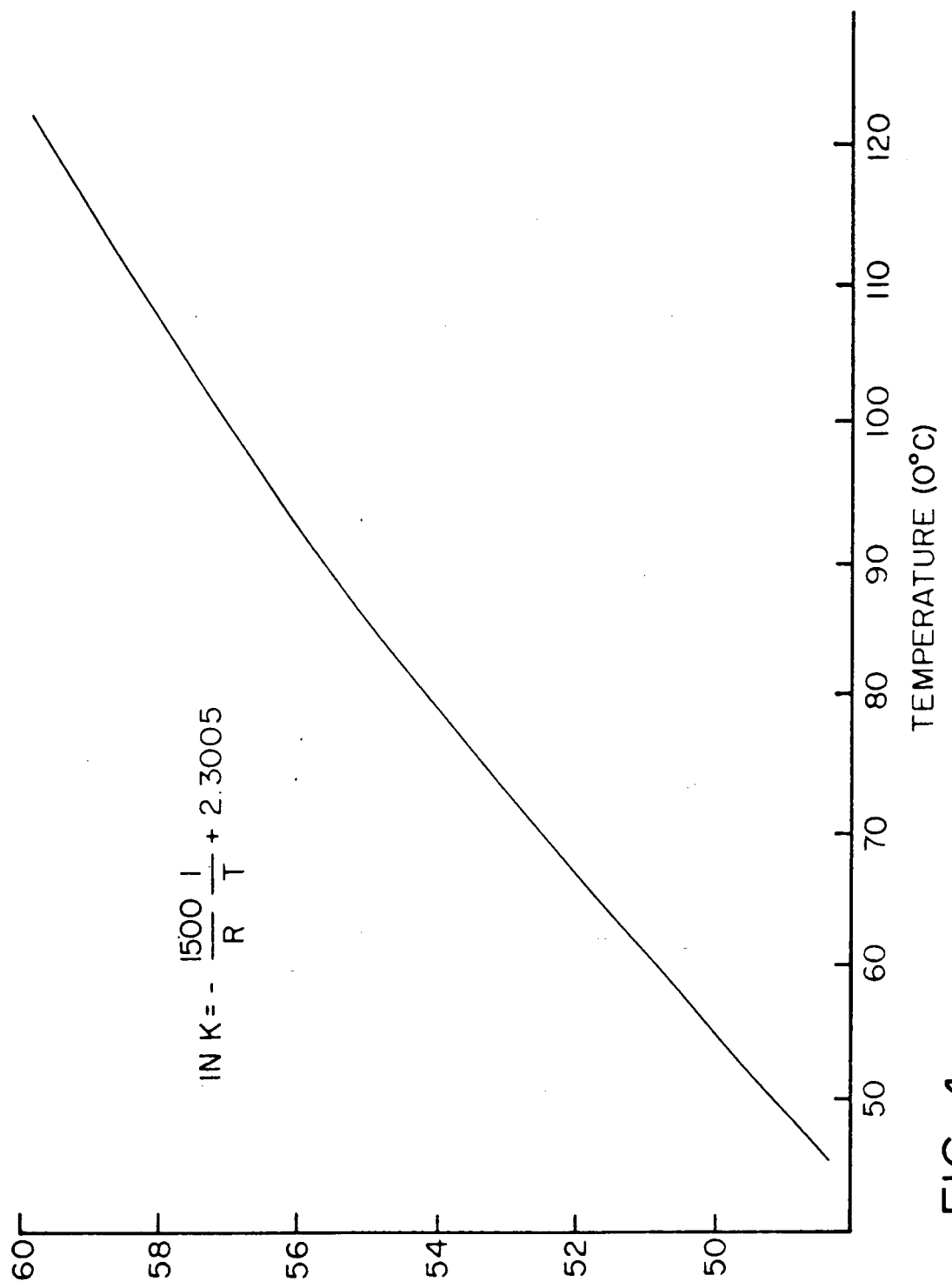
FIG. 4 is a graph depicting the effect of temperature on the glucose/fructose equilibrium.

The activity function ($L_T$) at each temperature is calculated as follows:

$$LT = \ln \frac{(I_e)}{I_e - I_T}$$

where $I_e$ = equilibrium degree of isomerization at each temperature (FIG. 4).

The relative activity ($A_r$) at each of the test temperature is calculated as follows:

$$A_r = (L_T/L_R) \cdot (k_{fr}/k_{fl})$$

LT = activity function at test temperature
L$_R$ = activity function at reference temperature
The best reference temperature is about 10° C. below the temperature at which 50% of maximum activity is displayed.
k$_{fT}$ = isomerization rate constant calculated at the test temperature (see formula below)
k$_{fR}$ = isomerization rate constant calculated at the reference temperature (see formula below)

$$k_f = exp(-6654/(T + 273) - 15.957)$$

where T is test (or reference) temperature in ° C.

Figure 5:
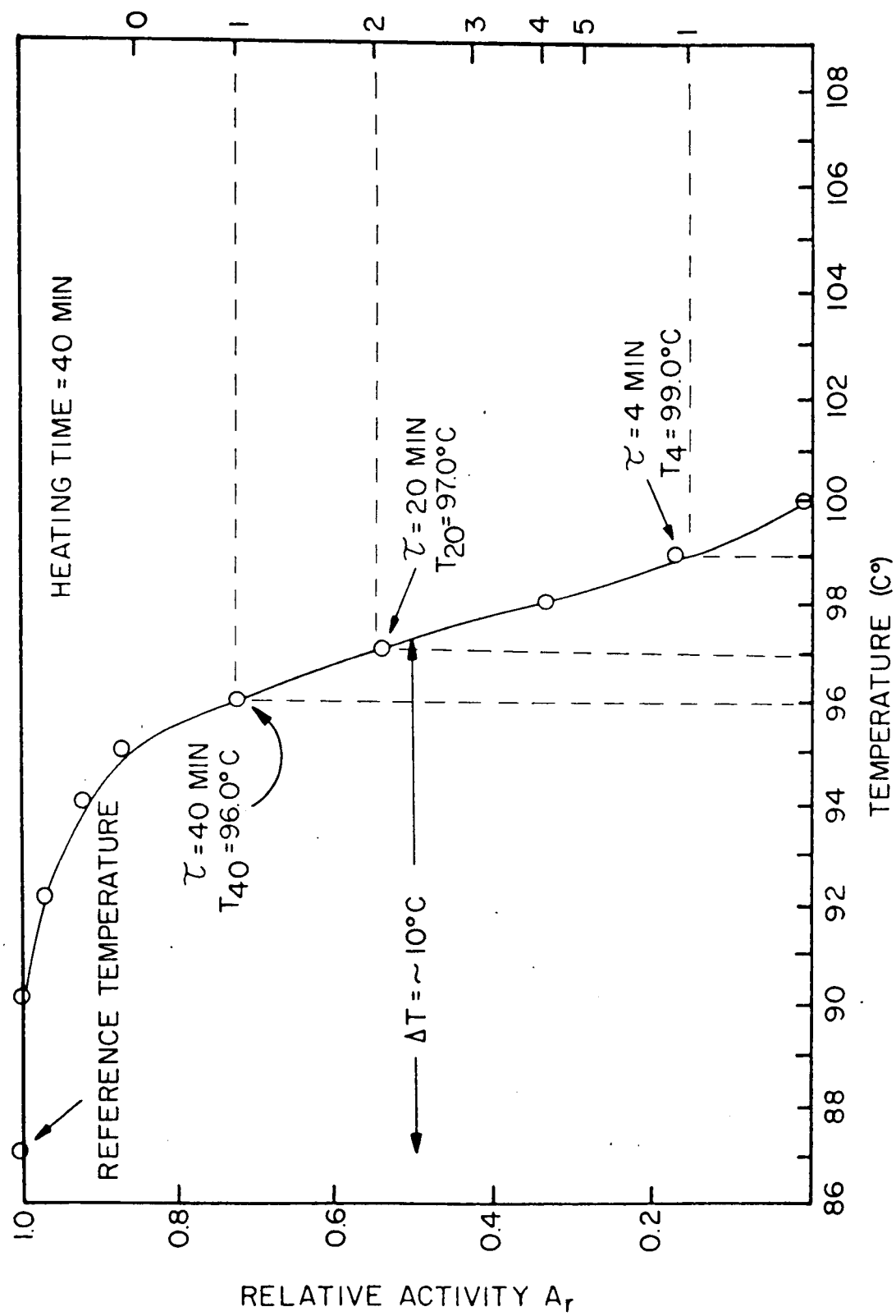
FIG. 5 is a graph of relative activity of *Streptomyces rubiginosus* XI as a function of temperature.

Relative activity is plotted vs. temperature as shown in FIG. 5. Relative activity is related to heating time and to enzyme half-life according to the following relationship:

$$A_r = \frac{(1 - 0.5^n)}{0.693n}$$

where $$n = \frac{t}{T}$$

t = heating time (40 minutes)
T = enzyme half-life (minutes)
Graphs of relative activity vs. temperature supply information on half-life. Thus, interpolation as shown on the graph in FIG. 5 identifies the temperature at which the half-life is 4, 20 or 40 minutes.

$T_{40} = 96.0°$ C.
$T_{20} = 97.0°$ C.
$T_4 = 99.0°$ C.

$T_{20}$ is reported to the nearest 0.1° C. as a standard expression of thermostability.

The $T_{20}$ value, the temperature at which the reference or the mutein has a 20 minute half-life, is a sensitive measure of an enzyme's thermostability. Relative to the reference XI thermostabilized muteins should retain more catalytic activity at elevated temperatures. Consequently, a thermostabilized mutein will have a larger $T_{20}$ value (it will demonstrate a 20 minute half-life at a temperature at least 1° C. higher than the reference enzyme). Quantitation of enzymatic activity to assess thermostability has the advantage of testing both the reversible (conformational) and irreversible (conformational plus chemical) thermoinactivation mechanisms. Many point mutations have been shown to result in muteins that are 2° C.-5° C. more stable than the parent enzyme. Because the precision of the $T_{20}$ test can be as low as ±0.1° C., thermostable xylose isomerase muteins are clearly identified by the $T_{20}$ method.

Use of Xylose Isomerase Muteins

The recombinantly produced *S. rubiginosus* xylose isomerase and muteins set forth herein may be used to convert glucose to fructose or xylose to xylulose in various industrial processes. The various muteins may be resistant to various inactivation reactions and more stable, under extreme conditions of temperature and pH, than native XI. In addition, $k_{cat}$ may be increased, $K_S$ may be decreased, $k_{catr}$ may be decreased and/or $K_p$ may be increased.

Deposits

On Aug. 5, 1987, Applicants deposited with the American Type Culture Collection, Rockville, Md, USA (ATCC) the mutein expression vector pTW11 in *E. coli* DG101 XI- accession no. 67,489. This deposit was made under the provisions of the Budapest Treaty on the International Recognition of the Deposit it of Microorganisms for the Purpose of Patent Procedure and the Regulations thereunder (Budapest Treaty). This assures maintenance of a viable culture for 30 years from the date of deposit. The deposit will be made available by ATCC under the terms of the Budapest Treaty, and subject to an agreement between Applicants and ATCC which assures permanent and unrestricted availability upon issuance of the pertinent U.S. patent. The Assignee herein agrees that if the culture on deposit die or is lost or destroyed when cultivated under suitable conditions, it will be promptly replaced upon notification with a viable specimen of the same culture. Availability of the deposit is not to be construed as a license to practice under the authority of any government in accordance with its patent laws.

This deposit was made for the convenience of the relevant public and does not constitute an admission that a written description would not be sufficient to permit practice of the invention or an intention to limit the invention to these specific constructs. Set forth hereinabove is a complete written description enabling a practitioner of ordinary skill to duplicate the construct deposited and to construct alternative forms of DNA, or organisms containing it, which permit the practice of the invention as claimed.

As will be apparent to those skilled in the art in which the invention is addressed, the present invention may be embodied in forms other than those specifically disclosed above without departing from the spirit or essential characteristics of the invention. The particular embodiments of the present invention described above, are, therefore, to be considered in all respects as illustrative and not restrictive. The scope of the present invention is as set forth in the appended claims rather than being limited to the examples contained in the foregoing description.

What is claimed is:

1. *Streptomyces rubiginosus* xylose isomerase having a substitution in the native amino acid sequence from Alanine$_{136}$ to Phenylalanine$_{136}$.

* * * * *

UNITED STATES PATENT AND TRADEMARK OFFICE
CERTIFICATE OF CORRECTION

PATENT NO. : 5,041,378
DATED : August 20, 1991
INVENTOR(S) : Drummond et al.

It is certified that error appears in the above-indentified patent and that said Letters Patent is hereby corrected as shown below:

In Figure 1, in the legend, change "TRANSMISSION" to --TRANSCRIPTION-- .

In Figure 4, insert along the Y-axis of the graph --PERCENT FRUCTOSE AT EQUILIBRIUM--.

Column 16, line 17, change "*rubiginosis*" to --*rubiginosus*--.

Column 16, line 60, change "moved" to --removed--.

Column 17, line 65, change "changes" to --chances--.

Column 17, line 67, insert --$\mu$-- after "0.45 or 0.20".

Column 37, line 56, insert a hyphen before the numeral 3, and a prime sign --'-- after the numeral 3.

Column 37, line 59, change "T'-T'CGCCGCGCGGCTCCTTCGGCTTGGGCTCG-3'" to --5'-CGCCGCGCGGCTCCTTCGGCTTGGGCTCG-3'--.

Column 42, line 28, change "LT" to --$L_T$--.

UNITED STATES PATENT AND TRADEMARK OFFICE
CERTIFICATE OF CORRECTION

PATENT NO. : 5,041,378

DATED : August 20, 1991

INVENTOR(S) : Drummond et al

It is certified that error appears in the above-indentified patent and that said Letters Patent is hereby corrected as shown below:

In Figure 4, change "IN K" to --ln K-- in the equation printed on the graph.

Column 1, lines 41 and 42, change "Streptomyces" to --*Streptomyces*--.

Column 3, line 24, change "T4lysozyme" to --T4 lysozyme--.

Column 10, line 23, delete "r" after "*Agrobacterium tumefaciens*".

Column 10, line 43, delete "25" before "Maniatis et al.".

Col. 11, line 62, change "$_6$mM dtt" to --6 mM DTT--.

Column 12, line 62, change "32YP" to --32$\gamma$P--.

Column 23, line 58, change "Streptomyces" to --*Streptomyces*--.

Column 29, line 18, begin a new line after the semicolon.

Column 32, line 12, insert --the following oligonucleotide primers to change alpha-helical--.

Column 35, line 54, change "$Val_{121}$" to --$Val_{21}$--.

Column 37, line 29, change "$Val_{1185}$" to --$Val_{185}$--.

Column 38, line 8, change 2 occurrences of "$Val_{1227}$" to --$Val_{227}$--.

Column 38, line 45, change 2 occurrences of "$Val_{1234}$" to --$Val_{234}$--.

UNITED STATES PATENT AND TRADEMARK OFFICE
CERTIFICATE OF CORRECTION

PATENT NO. : 5,041,378
DATED : August 20, 1991
INVENTOR(S) : Drummond et al

It is certified that error appears in the above-indentified patent and that said Letters Patent is hereby corrected as shown below:

Column 39, line 13, change 2 occurrences of "$Val_{1256}$" to --$Val_{256}$--.
Column 42, line 36, change "LT" to --$L_T$--.
Column 42, line 61, change "Y" to --T--.

Signed and Sealed this

Third Day of August, 1993

Attest:

MICHAEL K. KIRK

*Attesting Officer*   Acting Commissioner of Patents and Trademarks